US008338373B2

(12) United States Patent
Carter

(10) Patent No.: US 8,338,373 B2
(45) Date of Patent: *Dec. 25, 2012

(54) METHOD FOR REDUCING THE RISK OF SPONTANEOUS ABORTION IN A HUMAN FEMALE SUBJECT

(75) Inventor: Darryl L. Carter, Owings Mills, MD (US)

(73) Assignee: Nora Therapeutics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/606,664

(22) Filed: Oct. 27, 2009

(65) Prior Publication Data

US 2010/0080837 A1  Apr. 1, 2010

Related U.S. Application Data

(63) Continuation-in-part of application No. 12/433,999, filed on May 1, 2009, now abandoned, which is a continuation-in-part of application No. 12/238,977, filed on Sep. 26, 2008, now abandoned, which is a continuation of application No. 11/411,361, filed on Apr. 24, 2006, now Pat. No. 7,470,662, and a continuation of application No. PCT/US2004/035468, filed on Oct. 25, 2004.

(60) Provisional application No. 60/514,472, filed on Oct. 24, 2003.

(51) Int. Cl.
*A61K 38/00* (2006.01)
*A61K 45/00* (2006.01)

(52) U.S. Cl. .......................... 514/9.8; 424/85.1; 530/351

(58) Field of Classification Search ..................... None
See application file for complete search history.

(56) References Cited

U.S. PATENT DOCUMENTS

| | | |
|---|---|---|
| 4,554,101 A | 11/1985 | Hopp |
| 5,104,651 A | 4/1992 | Boone et al. .................. 424/85.1 |
| 5,147,799 A | 9/1992 | Bursuker et al. ........... 435/240.1 |
| 5,276,017 A | 1/1994 | Feinberg et al. |
| 5,284,656 A | 2/1994 | Platz et al. |
| 5,320,840 A | 6/1994 | Camble et al. |
| 5,399,345 A | 3/1995 | Schumacher et al. |
| 5,416,195 A | 5/1995 | Camble et al. |
| 5,422,248 A | 6/1995 | Smith et al. |
| 5,766,944 A | 6/1998 | Ruiz |
| 5,837,230 A | 11/1998 | Nakai et al. |
| 5,888,495 A | 3/1999 | Schrier et al. |
| 5,891,429 A | 4/1999 | Clark et al. |
| 5,895,646 A | 4/1999 | Wang |
| 5,908,763 A | 6/1999 | Clark et al. |
| 5,919,757 A | 7/1999 | Michaelis et al. |
| 5,981,551 A | 11/1999 | Luengo et al. |
| 5,989,537 A | 11/1999 | Holly et al. |
| 6,040,340 A * | 3/2000 | Chwalisz et al. ............ 514/509 |
| 6,150,085 A | 11/2000 | Hess et al. |
| 6,162,417 A | 12/2000 | Goodman et al. |
| 6,162,427 A | 12/2000 | Baumann et al. |
| 6,166,183 A | 12/2000 | Ishikawa et al. |
| 6,261,550 B1 | 7/2001 | Osslund |
| 6,277,379 B1 | 8/2001 | Oaks et al. ............... 424/197.11 |
| 6,565,841 B1 | 5/2003 | Niven et al. |
| 6,646,110 B2 | 11/2003 | Nissen et al. |
| 6,946,548 B2 | 9/2005 | Sarkar et al. .................. 530/399 |
| 6,979,674 B1 | 12/2005 | Goldenberg et al. ........... 514/12 |
| 2001/0009922 A1 | 7/2001 | Faller et al. |
| 2002/0086296 A1 | 7/2002 | Meyers ............................. 435/6 |
| 2003/0068664 A1 | 4/2003 | Albitar et al. |
| 2004/0105858 A1 | 6/2004 | Kim et al. |
| 2004/0137557 A1 | 7/2004 | DeFrees et al. |
| 2004/0224393 A1 | 11/2004 | Kwon et al. |
| 2009/0035263 A1 | 2/2009 | Carter |

FOREIGN PATENT DOCUMENTS

| | | | |
|---|---|---|---|
| WO | WO2005/039505 A2 | 5/2005 | |
| WO | WO2006/128176 A2 | 11/2006 | |
| WO | WO2006128176 A2 | 11/2006 | |
| WO | WO2008/009705 A1 | 1/2008 | |

OTHER PUBLICATIONS

Scarpellini et al., Fertility and Sterility, vol. 80, Suppl. 3, pp. S288, 2003.*
Clark et al., Human Reproduction Update. 7: 501-511, 2001.*
Reidhaar-Olson JF, et al., "Identification of Residues Critical to the Activity of Human Granulocyt Colony-Stimulating Factor", Biochemistry, Jul. 16, 1996; 35(28): 9034-9041.
Sun, et al., "IFN-γ Promotes Apoptosis of the Uterus and Placenta in Pregnant Rat and Human Cytotrophoblast Cells", Journal of Interferon Cytokine Research, Jul. 2007; 27(7): 567-578.
Lecoeur H, et al., "Strategies for phenotyping apoptotic peripheral human lymphocytes comparing ISNT, annexin-V and 7-AAD cytofluorometric staining methods", Journal of Immunological Methods, Dec. 1, 1997; 209(2): 111-123.
Delgrave, et al., "Recursive Ensemble Mutagenesis", Protein Engineering 6, 1193; (3):327-331.
International Search Report and Written Opinion of the International Searching Authority (International Application No. PCT/US2009/042481, filed May 1, 2009).
International Search Report and Written Opinion of the International Searching Authority (International Application No. PCT/US2009/062321, filed Oct. 28, 2009).
Arpaci et al., "A Successful and Simplified Filgrastim Primed Single Apheresis Method Without Large Volume Apheresis for Peripheral Blood Stem Cell Collection," *Jpn J Clin Oncol* 30(3): 153-158, 2000.
Berenson et al., "Transplantation of CD34+ Hematopoietic Progenitor Cells," *Cancer Investigation* 14(6): 589-596, 1996.

(Continued)

*Primary Examiner* — Gyan Chandra
(74) *Attorney, Agent, or Firm* — Seed IP Law Group PLLC

(57) ABSTRACT

Methods and kits for preventing or reducing the likelihood of implantation failure or spontaneous abortion in a recipient of FET, ICSI, GIFT or ZIFT are provided. The methods include administering into a recipient of FET, ICSI, GIFT or ZIFT in need of such treatment an effective amount of granulocyte colony stimulating factor (G-CSF).

19 Claims, No Drawings

OTHER PUBLICATIONS

Bueno et al., "Endoscopic placement of direct percutaneous jejunostomy tubes in patients with complications after esophagectomy," *Gastrointest Endosc* 57(4): 536-540, 2003.

Calhoun et al., "A randomized pilot trial of administration of granulocyte colony-stimulating factor to women before preterm delivery," *Am J Obstet Gynecol* 179(3, Pt 1): 766-771, 1998.

Cameo et al., "Similar embryotoxic effects of sera from infertile patients and exogenous interferon-γ on long-term in-vitro development of mouse embryos," *Human Reproduction* 14(4): 959-963, 1999.

Cavallaro et al., "Three to six year follow-up of normal donors who received recombinant human granulocyte colony-stimulating factor," *Bone Marrow Transplantation* 25: 85-89, 2000.

Chaouat et al., "Implantation: can immunological parameters of implantation failure be of interest for preeclampsia?" *J Reproductive Immunology* 59: 205-217, 2003.

Clark et al., "Prevention of Spontaneous Abortion in DBA/2-Mated CBA/J Mice by GM-CSF Involves $CD8^+T$ Cell-Dependent Suppression of Natural Effector Cell Cytotoxicity against Trophoblast Target Cells," *Cellular Immunology* 154: 143-152, 1994.

Deng et al., "Site-Directed Mutagenesis of Virtually Any Plasmid by Eliminating a Unique Site," *Analytical Biochemistry* 200: 81-88, 1992.

Doncarli et al., "Conversion in vivo from an eaerly dominant Th0/Th1 response to a Th2 phenotype during the development of collagen-induced arthritis," *Eur J Immunol* 27: 1451-1458, 1997.

Dreger et al., "G-CSF-mobilized peripheral blood progenitor cells for allogeneic transplantation: safety, kinetics of mobilization, and composition of the graft," *British Journal of Haematology* 87: 609-613, 1994.

Duan, "Production of Granulocyte Colony Stimulating Factor in Decidual Tissue and its Significance in Pregnancy," *Osaka City Medical Journal* 36(2): 81-97, 1990.

Dudrick et al., "Total Parenteral Nutrition: Techniques, Complications, and Prevention," *Surgical Technology International VII*, pp. 174-184, 1998.

Fukunaga et al., "Purification and Characterization of the Receptor for Murine Granulocyte Colony-stimulating Factor," *J Biol Chem* 265(23): 14008-14015, 1990.

Griebel et al., "Management of Spontaneous Abortion," *Am Fam Physician* 72(7): 1243-1250, 2005.

Huang et al., "Maintaining hyporesponsiveness and polarization potential of T cells after in vitro mixture of G-CSF mobilized peripheral blood grafts and G-CSF primed bone marrow grafts in different proportions," *Transplant Immunology* 17: 193-197, 2007.

Kocherlakota et al., "Preliminary Report: rhG-CSF May Reduce the Incidence of Neonatal Sepsis in Prolonged Preeclampsia-associated Neutropenia," *Pediatrics* 102(5): 1107-1111, 1998.

Kozak, "At Least Six Nucleotides Preceding the AUG Initiator Codon Enhance Translation in Mammalian Cells," *J Mol Biol* 196: 947-950, 1987.

Krishnan et al., "T Helper 1 Response Against *Leishmania major* in Pregnant C57BL/6 Mice Increases Implantation Failure and Fetal Resorptions," *The Journal of Immunology* 156: 653-662, 1996.

Kwak-Kim et al., "Increased T helper 1 cytokine responses by circulating T cells are present in women with recurrent pregnancy losses and in infertile women with multiple implantation failures after IVF," *Human Reproduction* 18(4): 767-773, 2003.

Link et al., "CD34 Positive Blood Cells for Allogeneic Progenitor and Stem Cell Transplantation," *Leukemia and Lymphoma* 26: 451-465, 1997.

Matsubara et al., "Concentrations of Serum Granulocyte-Colony-Stimulating Factor in Normal Pregnancy and Preeclampsia," *Hypertension in Pregnancy* 18(1): 95-106, 1999.

Mauri et al., "Relationship between Th1/Th2 cytokine patterns and the arthritogenic response in collagen-induced arthritis," *Eur J Immunol* 26: 1511-1518, 1996.

Medlock et al., "Granulocyte Colony-Stimulating Factor Crosses the Placenta and Stimulates Fetal Rat Granulopoiesis," *Blood* 81(4): 916-922, 1993.

The Merck Manual of Diagnosis and Therapy, Beers and Berkow, eds., 17th ed., Merck Research Laboratories, Whitehouse Station, NJ, 1999, p. 1995.

The Merck Manual of Diagnosis and Therapy, Beers and Berkow, eds., 17th ed., Merck Research Laboratories, Whitehouse Station, NJ, 1999, pp. 2053-2061.

Mohandas et al., "Total parenteral nutrition," *Natl Med J India* 16(1): 29-33, 2003.

Mori et al, "Immunomolecular Mechanisms in Mammalian Implantation," *Endocrine Journal* 41(Suppl): S17-S31, 1994.

Morris et al., "Stem cell mobilization with G-CSF analogs: a rational approach to separate GVHD and GVL?" *Blood* 107(9): 3430-3435, 2006.

Movérare et al., "Study of the Th1/Th2 balance, including IL-10 production, in cultures of peripheral blood mononuclear cells from birch-pollen-allergic patients," *Allergy* 55: 171-175, 2000.

Okkels, "A URA3-Promoter Deletion in a pYES Vector Increases the Expression Level of a Fungal Lipase in *Saccharomyces cerevisiae*," *Ann Ny Acad Sci* 782: 202-207, 1996.

Oksenberg et al., "In vitro suppression of murine blastocysts growth by sera from women with reproductive disorders," *Am J Reprod Immunol Microbiol* 11(4): 118-124, 1986.

Papadimitriou et al., "Non-Cryopreserved Peripheral Blood Progenitor Cells Collected by a Single Very Large-Volume Leukapheresis: A Simplified and Effective Procedure for Support of High-Dose Chemotherapy," *J Clin Apheresis* 15: 236-241, 2000.

Perricone et al., "GM-CSF and Pregnancy: Evidence of Significantly Reduced Blood Concentrations in Unexplained Recurrent Abortion Efficiently Reverted by Intravenous Immunoglobulin Treatment," *AJRI* 50: 232-237, 2003.

Raghupathy et al., "Maternal Th1- and Th2-Type Reactivity to Placental Antigens in Normal Human Pregnancy and Unexplained Recurrent Spontaneous Abortions," *Cellular Immunology* 196: 122-130, 1999.

Raghupathy et al., "Cytokine production by maternal lymphocytes during normal human pregnancy and in unexplained recurrent spontaneous abortion," *Human Reproduction* 15(3): 713-718, 2000.

Raziuddin et al., "Divergent Cytokine Production Profile in Behçet's Disease. Altered Th1/Th2 Cell Cytokine Pattern," *J Rheumatol* 25(2): 329-333, 1998.

Reidhaar-Olson et al., "Random Mutagenesis of Protein Sequences Using Oligonucleotide Cassettes," *Methods in Enzymology* 208: 564-586, 1991.

Rezaei et al., "T-helper (1) cytokines increase during early pregnancy in women with a history of recurrent spontaneous abortion," *Med Sci Monit* 8(8): CR607-CR610, 2002.

Roussev et al., "Validation of an embryotoxicity assay," *Am J Reprod Immunol* 33(2): 171-175, 1995.

Saito et al., "Elevation of Amniotic Fluid Interleukin 6 (IL-6), IL-8 and Granulocyte Colony Stimulating Factor (G-CSF) in Term and Preterm Parturition," *Cytokine* 5(1): 81-88, 1993.

Sanger et al., "DNA sequencing with chain-terminating inhibitors," *Proc Natl Acad Sci USA* 74(12): 5463-5467, 1977.

Sbracia et al., "Use of GM-CSF 1 in the Treatment of Habitual Abortion: a Pilot Study," *Fertility & Sterility* 70(3, Suppl. 1): S62-S63, 1995.

Scarpellini et al., "Effectiveness of GM-CSF 1 in the Treatment of Habitual Abortion in a Controlled Study," *AJRI (Abstract)* 51: 433-434, 2004.

Schust et al., "Correlation of Serum Cytokine and Adhesion Molecule Determinations With Pregnancy Outcome," *J Soc Gynecol Invest* 3(5): 259-261, 1996.

Shike et al., "Direct percutaneous endoscopic jejunostomies for enteral feeding," *Gastrointest Endosc* 44(5): 536-540, 1996.

Stemmer et al., "Single-step assembly of a gene and entire plasmid from large numbers of oligodeoxyribonucleotides," *Gene* 164: 49-53, 1995.

Stephenson et al., "Evaluation and Management of Recurrent Early Pregnancy Loss," *Clin Obstet Gynecol* 50(1): 132-145, 2007.

Sullivan et al., "Recurrent Fetal Aneuploidy and Recurrent Miscarriage," *Obstet Gynecol* 104(4): 784-788, 2004.

Thomason et al., "Prevalence of embryotoxic factor in sera from women with unexplained recurrent abortion," *Am J Reprod Immunol* 34(6): 338-341, 1995.

Vogel et al., "Clinical Applications of CD34+ Peripheral Blood Progenitor Cells (PBPC)," *Stem Cells* 18: 87-92, 2000.

Wells et al., "Cassette mutagenesis: an efficient method for generation of multiple mutations at defined sites," *Gene* 34: 315-323, 1985.

Wörfel et al., "Approaches to a Better Implantation," *J Assisted Reproduction and Genetics* 17(8): 473, 2000.

Xing et al., "Th1/Th2 type cytokines in hepatitis B patients treated with interferon-α," *Chin Med J* 114(9): 921-924, 2001.

Yabuki et al., "Giant Lysosomes in the Renal Proximal Tubules—A Morphological Characteristic of DBA/2 and DBA/1 Mouse Kidneys," *Exp Anim* 52(2): 159-163, 2003.

Younghusband et al., "Mutagenesis of conserved 5' elements and transcription of a chicken H1 histone gene," *Nucleic Acids Research* 14(2): 635-644, 1986.

Zell et al., "DNA mismatch-repair in *Escherichia coli* counteracting the hydrolytic deamination of 5-methyl-cytosine residues," *The EMBO Journal* 6(6): 1809-1815, 1987.

European Search Report dated May 4, 2010 for EP Application No. 10155704.9 (3 pages).

Supplementary European Search Report dated Jun. 10, 2009 for EP Application No. 04796441.6 (6 pages).

Written Opinion of the International Searching Authority dated Sep. 18, 2007 for PCT/US04/35468 (4 pages).

International Search Report dated Oct. 19, 2007 for PCT/US04/35468 (5 pages).

International Preliminary Report on Patentability and Written Opinion dated Nov. 6, 2007 for PCT/US2004/035468 (5 pages).

International Search Report dated Jan. 29, 2010 for PCT/US2009/042481 (4 pages).

International Search Report dated May 28, 2010 for PCT/US2009/062321 (6 pages).

Kaufmann et al., "Term delivery in a woman with severe congenital neutropenia, treated with growth colony stimulating factor," *Human Reproduction* 13(2): 498-499, 1998.

\* cited by examiner

METHOD FOR REDUCING THE RISK OF SPONTANEOUS ABORTION IN A HUMAN FEMALE SUBJECT

This application is a continuation-in-part application of U.S. patent application Ser. No. 12/433,999, filed May 1, 2009, which is a continuation-in-part application of U.S. patent application Ser. No. 12/238,977, filed Sep. 26, 2008, which is a continuation application of Ser. No. 11/411,361, now U.S. Pat. No. 7,470,662, filed Apr. 24, 2006 which is a continuation application of PCT/US04/35468, filed Oct. 25, 2004, which claims priority from U.S. Provisional Application Ser. No. 60/514,472, filed Oct. 24, 2003. The entirety of all of the aforementioned applications is incorporated herein by reference.

This is an incorporation by reference of the material in the ASCII text file filed concurrently herewith, specifically 70200SequenceListing.txt, created on Oct. 27, 2009 with a size of 1,924 bytes.

FIELD

The present invention generally relates to methods of preventing implantation failure or miscarriage during assisted reproduction and, in particular, to methods for reducing the likelihood of or preventing implantation failure or spontaneous abortion in recipients of FET, ICSI, GIFT and ZIFT.

BACKGROUND

Accompanying the rising age of hopeful parents is the increasing use of assisted reproductive techniques such as frozen embryo transfer (FET), intracytoplasmic sperm injection (ICSI), gamete intrafallopian tube transfer (GIFT), and zygote intrafallopian tube transfer (ZIFT). All these techniques, however, require proper implantation of the embryo and full term development to achieve a successful pregnancy.

Implantation and placentation are complex processes involving hormonal, immune, and anatomical changes in the mother and migration and cellular division of the embryo. Various uterine pathologies, such as thin endometrium, altered expression of adhesive molecules and immunological factors, may be the causes for repeated implantation failure.

Spontaneous abortion occurs in 15%-50% of diagnosed pregnancies in women between fifteen and forty-five years of age. The formal definition of recurrent spontaneous abortion is three or more spontaneous abortions. However, the American College of Obstetrics and Gynecology recommends that in women over the age of 35, a thorough workup should be undertaken after two spontaneous abortions. Approximately 3-4% of women are estimated to fit the formal definition of recurrent spontaneous abortion. The risk of pregnancy loss increases from 15-20% in the first pregnancy to 40% after one spontaneous abortion.

Although many pregnancies lost in the first trimester are due to fetal causes; spontaneous abortion, the loss of the products of conception prior to the $20^{th}$ week of pregnancy, is often a disorder of unknown etiology. It has been theorized that spontaneous abortions are a natural rejection of a fetus with abnormalities incompatible with life; however, this theory has yet to be substantiated.

Risk factors for spontaneous include age, weight and overall health of the woman. The prevalence of spontaneous abortion increases with increasing maternal age, although not with gravidity. The risk begins to increase rapidly at age 35 years. The risk of spontaneous abortion at age 40 is approximately twice that at age 20. As families are planned later and later in life, the frequency of spontaneous abortion will only increase without effective methods of prevention.

Threatened abortion generally presents as cramping and bleeding for which treatment is bed rest. This conservative treatment provides palliative care for the mother but does little to alter the outcome. The use of hormones is generally contraindicated due to the risk of congenital anomalies, including malformation of the vessels of the heart of the embryo and possible genital abnormalities in female offspring.

In addition to the physical toll of these disorders, the loss of a desired pregnancy takes a tremendous emotional toll on hopeful and expectant parents. Loss of a pregnancy can lead to feelings of inadequacy, hopelessness and guilt which can have a devastating effect on individuals and on a marriage.

New methods and compositions are always needed to reduce risks associated with pregnancy to the health of the mother and fetus. Effective prevention of implantation failure or spontaneous abortion can allow women, especially women at risk, to have successful pregnancies. In particular, effective prevention of these disorders in women who suffer from infertility can allow women, especially women who seek medical care in the form of assisted reproduction like FET, ICSI, GIFT and ZIFT to have successful pregnancies. Prevention of implantation failure during assisted reproduction allows successful pregnancies, reduces the risks to women, and saves time and money.

SUMMARY

One objective of the present invention is to provide methods, compositions and kits comprising a granulocyte colony stimulating factor (G-CSF) or hG-CSF analog in an amount effective to prevent or reducing the likelihood of the spontaneous abortion or implantation failure in FET, ICSI, GIFT and ZIFT.

One aspect of the present invention relates to a method for preventing or reducing the likelihood of implantation failure or spontaneous abortion in a recipient of FET, ICSI, GIFT and ZIFT. The method comprises administering to the recipient of FET, ICSI, GIFT and ZIFT an effective amount of a composition comprising G-CSF or hG-CSF analog.

In another embodiment, the composition is administered parenterally, administered enterally, or topically.

In another embodiment, the composition is administered by inhalation.

In another embodiment, the composition is administered prior to the FET, ICSI, GIFT or ZIFT procedure.

In another embodiment, the FET, ICSI, GIFT or ZIFT procedure is preceded by a controlled ovarian hyperstimulation procedure, and the composition is administered before, during, or after the time of controlled ovarian hyperstimulation.

In another embodiment, the composition is administered daily for one to thirty-five consecutive days.

In another embodiment, the composition is administered daily until the end of the first trimester.

In another embodiment, the composition is administered daily until the recipient presents a normal Th1 response or a normal Th2 response or both.

In another embodiment, the G-CSF or hG-CSF analog is administered at a dose of between 0.1 mcg/kg/day to 600 mcg/kg/day.

In another embodiment, the G-CSF or hG-CSF analog is administered at a dose of between 0.5 mcg/kg/day to 300 mcg/kg/day.

In another embodiment, the G-CSF or hG-CSF analog is administered at a dose of between 1 mcg/kg/day to 100 mcg/kg/day.

In another embodiment, the G-CSF or hG-CSF analog is administered at a dose of between 1 mcg/kg/day to 50 mcg/kg/day.

In another embodiment, the G-CSF or hG-CSF analog is administered at a dose of between 1 mcg/kg/day to 10 mcg/kg/day.

In another embodiment, the G-CSF or hG-CSF analog is administered at a dose of between 1 mcg/kg/day to 2 mcg/kg/day.

In another embodiment, the G-CSF or hG-CSF analog is administered in the form of a nucleotide sequence encoding G-CSF or hG-CSF analog.

In another embodiment, the composition further comprises an additive selected from the group consisting of cytokines that suppress Th1 immune response, cytokines that enhance Th2 immune response, cytokines that support successful pregnancy through non-immunologic mechanisms, anti-inflammatory agents, and inhibitors of pro-inflammatory cytokines.

In another embodiment, the additive is selected from the group consisting of interferon alpha, interferon beta, macrophage colony stimulating factor (M-CSF), granulocyte macrophage colony stimulating factor (GM-CSF), leukemia inhibitory factor (LIF), transforming growth factor beta (TGF-beta), interleukin-1 (IL-1), IL-3, IL-4, IL-6, IL-7, IL-8, IL-9, IL-10, IL-11, IL-13, IL-14, IL-15, IL-19, IL-20, IL-21, IL-22, IL-24, IL-25, IL-26, IL-27, IL-28, IL-29, IL-30, IL-31, IL-32, IL-33, and IL-35.

In another embodiment, the composition further comprises a pharmaceutically acceptable carrier.

Another aspect of the present invention relates to a kit for preventing or reducing the likelihood of implantation failure and spontaneous abortion in a recipient in FET, ICSI, GIFT or ZIFT. The kit includes an effective amount of G-CSF or hG-CSF analog; and a label with instructions for using the G-CSF or hG-CSF analog to prevent or reduce the likelihood of implantation failure and spontaneous abortion.

Another aspect of the present invention provides methods of treating, preventing or reducing the risk of preeclampsia and preterm labor in a recipient of FET, ICSI, GIFT or ZIFT by administering to the recipient an effective amount of G-CSF, hG-CSF analog, or an effective amount of mobilized peripheral blood stem cells. Subjects at risk can be identified according to the methods described herein or according to methods known to practitioners in the art. Typically, the subject is in the second or third trimester of pregnancy.

DETAILED DESCRIPTION

The practice of the present invention will employ, unless otherwise indicated, conventional methods of molecular biology, cell biology, immunology, biochemistry, microbiology, gynecology and obstetrics within the skill of the art. Such techniques are explained fully in the literature. All publications, patents and patent applications cited herein, whether supra or infra, are hereby incorporated by reference in their entirety.

DEFINITIONS

As used herein, the following terms shall have the following meanings:

The terms "treat", "treating" or "treatment" as used herein, refers to a method of alleviating or abrogating a disorder and/or its attendant symptoms. The terms "prevent", "preventing" or "prevention", as used herein, refer to a method of barring a subject from acquiring a disorder and/or its attendant symptoms. In certain embodiments, the terms "prevent", "preventing" or "prevention" refer to a method of reducing the risk of acquiring a disorder and/or its attendant symptoms.

The term "spontaneous abortion" refers to delivery or loss of the product of conception before the 20th week of pregnancy. The term spontaneous abortion includes but is not limited to threatened abortion, inevitable spontaneous abortion, incomplete spontaneous abortion, habitual or recurrent spontaneous abortion or missed abortion.

The term "miscarriage" is synonymous with spontaneous abortion.

The term "threatened spontaneous abortion" refers to any bleeding or cramping of the uterus in the first 20 weeks of pregnancy.

The term "inevitable spontaneous abortion" refers to bleeding or rupture of the membranes accompanied by pain and dilation of the cervix.

The term "incomplete spontaneous abortion" refers to expulsion of part of the products of conception or rupture of the membranes.

The term "habitual spontaneous abortion" or "recurrent spontaneous abortion" refers to three or more consecutive spontaneous abortions.

The term "missed abortion" refers to delay in expulsion of a dead fetus.

The term "assisted reproduction" refers to clinical and laboratory techniques used to enhance fertility in humans and animals, including, but not limited to, FET, ICSI, GIFT, ZIFT and the like.

The term "implantation failure" refers to the failure of an embryo produced by assisted reproduction or through artificial insemination to implant or to implant normally in the uterus of a recipient subject.

The term "preeclampsia" refers the development of hypertension with albuminuria or edema typically between the 20th week of pregnancy and the end of the first week postpartum. Any pregnant subject who develops a blood pressure of 140/90 mm Hg or higher, edema of the face or hands, albuminuria of ≧1+ or whose blood pressure rises by 30 mm Hg systolic or 15 mm Hg diastolic (even if less than 140/90 mm Hg) is considered preeclamptic.

The term "colony stimulating factor" or "CSF" relates to a growth factor that promotes and contributes to the maturity of cells, such as, hematopoietic and blood cells. Examples of CSF molecules include, but are not limited to, erythropoietin, G-CSF, GM-CSF, macrophage CSF, interleukin (IL)-3, IL-6 and stem cell factor.

The term "granulocyte-colony stimulating factor" or "G-CSF" refers to compounds or factors that stimulate proliferation, differentiation, commitment and end cell functional activation of granulocytes in an animal, including a human subject. G-CSF includes derivatives, mimetics, variants and chemically modified compounds or hybrids thereof as described in U.S. Pat. Nos. 5,399,345; 5,416,195; 5,981,551; 6,166,183 and 6,261,550, the contents of which are incorporated by reference in entireties. G-CSF is commercially available under the names Neupogen® (Amgen), Tevagrastim® (Teva), Biograstim® (CT Arzneimittel), Ratiograstim® (Ratiophann GmbH)), Zarzio® (Sandoz GmbH), Filgrastim Hexal® (Hexal AG), Neulasta® (Amgen), Granocyte® and Neutrogin® (Chugai), and Neu-up® (Kyowa Hakko).

The term "granulocyte" refers to a white blood cell containing granules, especially a leukocyte (white blood cell or corpuscle) containing neutrophil, basophil or eosinophil granules in its cytoplasm.

The term "granulocyte/macrophage colony stimulating factor" or "GM-CSF" refers to compounds or factors that stimulate proliferation, differentiation, commitment and end cell functional activation of monocytes and granulocytes in an animal, including a human subject. GM-CSF includes derivatives, mimetics, variants and chemically modified compounds or hybrids thereof as described in, for example, U.S. Pat. Nos. 5,895,646; 5,891,429 and 5,908,763; the contents of which are incorporated by reference in entireties. GM-CSF is commercially available under the trade names Leukine®, Berlex® and Leucomax® (Wyeth).

The term "macrophage colony stimulating factor" or "M-CSF" (also known as "CSF-1") refers to compounds or factors that stimulate proliferation or promote survival of monocytes and macrophages in an animal, including a human subject. M-CSF includes derivatives, mimetics, variants and chemically modified compounds or hybrids thereof as described in, for example, U.S. Pat. Nos. 5,837,230 and 5,888,495; the contents of which are incorporated by reference in entireties. M-CSF is commercially available under the trade name Leukoprol® (Kyowa).

The term "macrophage" relates to a mononuclear, phagocytic white blood cell that can exit the circulation and enter tissue spaces.

The term "therapeutically effective amount" refers to that amount of an active agent being administered sufficient to prevent development of or alleviate to some extent one or more of the symptoms of the condition or disorder being treated.

The term "preterm labor" also known as premature labor, refers to the beginning of regular contractions that cause the cervix to begin dilation and effacement before the 37th week of pregnancy.

The term "effective amount" refers to that amount of an active agent being administered sufficient to prevent the disorder or prevent one or more symptoms of the disorder being treated. In certain embodiments, the term "effective amount" refers to that amount of an active agent being administered sufficient to reduce the risk of the disorder or one or more symptoms of the disorder.

The term "subject" refers to animals such as mammals, including, but not limited to, primates (such as humans), cows, sheep, goats, horses, dogs, cats, rabbits, rats, mice and the like. In preferred embodiments, the subject is a human female.

The term "label" refers to a display of written, printed or graphic matter on the immediate container of an article, for example the written material displayed on a vial containing a pharmaceutically active agent.

The term "labeling" refers to all labels and other written, printed or graphic matter on any article or any of its containers or wrappers or accompanying such article, for example, a package insert or instructional videotapes or computer data storage devices, such as CDs and DVDs, accompanying or associated with a container of a pharmaceutically active agent.

hG-CSF Analog

One aspect of the present invention is directed to an hG-CSF analog comprising an amino acid sequence that differs from the sequence in SEQ ID NO:1 at position 17 and at least another position, wherein said analog is capable of inhibiting trophoblast cell apoptosis.

In one embodiment, the hG-CSF analog comprises a polypeptide sequence that differs from the sequence in SEQ ID NO:1 at positions 17 and 38, and at least another position.

In another embodiment, the hG-CSF analog comprises a polypeptide sequence that differs from the sequence in SEQ ID NO:1 at positions 17, 38 and 58.

In another embodiment, the hG-CSF analog comprises a polypeptide sequence that differs from the sequence in SEQ ID NO:1 at positions 17, 38 and 53.

In another embodiment, the hG-CSF analog contains, at position 17, an amino acid selected from the group consisting of leucine, methionine, glutamine, tryptophane, alanine, tyrosine, serine, lysine, glutamine, threonine, asparagine, and histidine.

In another embodiment, the hG-CSF analog contains a substitution at position 38.

In another embodiment, the hG-CSF analog contains a substitution at position 53.

In another embodiment, the hG-CSF analog contains a substitution at position 58.

In another embodiment, the hG-CSF analog of the present invention contains substitutions that are made in amino acids that are on the surface of the protein and that are not involved in intramolecular hydrogen bonding. Preferred sites include positions 12, 16, 18, 23, 32, 33, 43, 44, 45, 46, 52, 57, 58, 71, 83, 90, 98, 101, 104, 108, 123, 137 and 159.

In another embodiment, the hG-CSF analog of the present invention contains substitutions that are made in amino acids that are on the surface of the protein and that are involved in intramolecular hydrogen bonding. Preferred sites include positions 22, 38, 39, 53, 77, 80, 93, 105, 115, 118, 122, 145 and 169.

The hG-CSF analog does not contain mutations that are known to disrupt the 3-dimensional conformation of G-CSF in a manner that impairs or reduces the affinity of G-CSF to its receptor, that impairs the ability of the G-CSF/G-CSF receptor complex to dimerize, or that significantly reduces the hG-CSF analog's stability (Reidhaar-Olson J F, et al., Biochemistry. 1996 Jul. 16; 35(28):9034-41). These excluded mutations will likely include mutations at the following 15 positions of SEQ ID NO:1, 15, 19, 25, 31, 34, 40, 47, 48, 49, 54, 112, 124, 142, 144 and 146.

A person of ordinary skill in the art would understand that modifications and changes can be made in the structure of the hG-CSF analog of the present invention and still obtain a molecule having desired biological activity (i.e., ability to inhibit trophoblast cell apoptosis). Because it is the interactive capacity and nature of a polypeptide that defines that polypeptide's biological activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art. It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is well-known in the art that an amino acid can be substituted by another amino acid having a similar hydropathic index and still obtains a functionally equivalent polypeptide. In such changes, the substitution of amino acids whose hydropathic indices are within +/−2 is preferred, those that are within +/−1 are particularly preferred, and those within +/−0.5 are even more particularly preferred. Substitution of like amino acids can also be made on the basis of hydrophilicity, particularly where the biological functional equivalent polypeptide, or polypeptide fragment, is intended for use in immunological embodiments. U.S. Pat. No. 4,554, 101, incorporated hereinafter by reference, states that the greatest local average hydrophilicity of a polypeptide, as governed by the hydrophilicity of its adjacent amino acids, correlates with its immunogenicity and antigenicity, i.e., with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below).

TABLE 1

Amino Acid Substitutions

| Original Residue | Exemplary Residue Substitution |
|---|---|
| Ala | Gly; Ser |
| Arg | Lys |
| Asn | Gln; His |
| Asp | Glu |
| Cys | Ser; Ala |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser; Ala |
| Trp | Tyr |
| Tyr | Trp; Phe |
| Val | Ile; Leu |

The hG-CSF analog of the present invention may contain non-conservative changes. In a preferred embodiment, variant polypeptides differ from a native sequence by substitution, deletion or addition of five amino acids or fewer. The hG-CSF analog may also (or alternatively) be modified by, for example, the deletion or addition of amino acids that have minimal influence on the immunogenicity, secondary structure, tertiary structure, and hydropathic nature of the polypeptide.

The hG-CSF analog also includes a polypeptide that is modified from the original polypeptide by either natural process, such as post-translational processing, or by chemical modification techniques which are well known in the art. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from post-translation natural processes or may be made by synthetic methods. Modifications include acetylation, acylation, ADP-ribosylation, amidation, covalent attachment of flavin, covalent attachment of a fluorophore or a chromophore, covalent attachment of a home moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

In one embodiment, the hG-CSF analog of the present invention is generated using an expression vector containing a polynucleotide sequence encoding the hG-CSF analog. The polynucleotide sequence encoding the hG-CSF analog is generated by introducing mutations into the coding sequence of a wild-type hG-CSF with standard techniques, such as site-directed mutagenesis and PCR-mediated mutagenesis. Alternatively, mutations can be introduced randomly along all or part of the coding sequence of the wild-type hG-CSF, such as by saturation mutagenesis, and the resultant mutants can be screened for biological activity to identify mutants that retain activity. Following mutagenesis, the hG-CSF analog can be expressed recombinantly and the activity of the protein can be determined.

In one embodiment, oligonucleotide primers are designed to introduce one or more amino acid mutations at the desired codon(s) of the coding sequence of the wild-type hG-CSF, which is cloned into an expression vector. Mutations will be confirmed by dideoxy DNA sequencing. Once DNA sequences have been confirmed, cells will be transfected with the expression vector. The expressed hG-CSF analog will be purified under conditions to minimize endotoxin contamination. A test for endotoxin will be performed by the *Limulus amebocyte* test. The hG-CSF analog will be tested for the ability to prevent apoptosis on JEG-3 cells exposed to recombinant human gamma interferon in in vitro culture. The detailed method will closely follow that of Sun, et al. (Sun Q H, et al., J. Interferon Cytokine Res. 2007 July; 27(7):567-78). Briefly, coriocarinoma cells (JEG or JAR-3 cell lines) will be exposed to recombinant human gamma interferon in vitro at a concentration that has been shown to induce apoptosis of cytotrophoblast cells (100 IU per ml) for 72 hours. The JEG or JAR-3 cells will be maintained in a chemically defined serum-free culture media and will be grown in Teflon 24-well plates to prevent them from adhering. After 72 hours, the cell suspensions will be harvested and washed three times in PBS. Cells will then be stained with Annexin V and 7-AAD for analysis of cell death by flow cytometry (Lecoeur H, et al., J. Immunol. Methods. 1997 Dec. 1; 209(2):111-23). Cells that are Annexin V positive and 7-AAD negative will be scored as apoptotic. Cells that are negative for both Annexin V and 7-AAD will be scored as viable. Cells that are positive for both Annexin V and 7-AAD will be scored as nectrotic. The relative activity (the ratio of viable to apoptotic cells) of the analogs at various concentrations will be compared to that of gamma interferon alone and to a pseudowildtype hG-CSF analog. The pseudowildtype hG-CSF analog will contain a single substitution of an alanine for the native cysteine at position 17.

Alternative to recombinant expression, the hG-CSF analog can be synthesized chemically using standard peptide synthesis techniques.

The hG-CSF analog of the present invention also includes fusion proteins. A fusion hG-CSF analog typically contains an hG-CSF analog-related polypeptide and a non-hG-CSF analog-related polypeptide. The hG-CSF analog-related polypeptide may correspond to all or a portion of an hG-CSF analog. In a preferred embodiment, the fusion hG-CSF analog comprises at least one biologically active portion of an hG-CSF analog. Within the fusion protein, the term “operatively linked” is intended to indicate that the hG-CSF analog-related polypeptide and the non-hG-CSF analog-related polypeptide are fused in-frame to each other. The non-hG-CSF analog-related polypeptide can be fused to the N-terminus or C-terminus of the hG-CSF analog-related polypeptide.

A peptide linker sequence may be employed to separate the hG-CSF analog-related from non-hG-CSF analog-related components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the hG-CSF analog-related peptide and non-hG-CSF analog-related polypeptide; and (3) the lack of hydrophobic or charged residues that might react with the polypeptide functional epitopes. Preferred peptide linker sequences contain gly, asn and ser residues. Other near neutral amino acids, such as thr and ala may also be used in the linker sequence. Amino acid sequences which may be used as linkers are well known in the art. The linker sequence may generally be from 1 to about 50 amino acids in length. Linker sequences are not required when the hG-CSF analog-related polypeptide and non-hG-CSF analog-related polypeptide have non-essential N-terminal amino acid regions that can be used to separate the functional domains and prevent steric interference.

For example, in one embodiment, the fusion protein is a glutathione S-transferase (GST)-hG-CSF analog fusion protein in which the hG-CSF analog sequences are fused to the C-terminus of the GST sequences. Such fusion proteins can facilitate the purification of recombinant hG-CSF analog.

In another embodiment, the fusion protein is an hG-CSF analog containing a heterologous signal sequence at its N-terminus. In certain host cells (e.g., mammalian host cells), expression and/or secretion of hG-CSF analogs can be increased through use of a heterologous signal sequence. Such signal sequences are well known in the art.

Preferably, an hG-CSF analog fusion protein of the invention is produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence. Moreover, many expression vectors are commercially available that already encode a fusion moiety (e.g., a GST polypeptide). An hG-CSF analog-encoding polynucleotide can be cloned into such an expression vector such that the fusion moiety is linked in-frame to the hG-CSF analog.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a polynucleotide sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods.

Alternatively, the signal sequence can be linked to the protein of interest using a sequence which facilitates purification, such as with a GST domain.

The hG-CSF analog of the present invention also includes polypeptide conjugates with hG-CSF activity. The conjugates comprise a polypeptide moiety and at least one non-polypeptide moiety. In one embodiment, the non-polypeptide moiety is a 2-6 polyethylene glycol moiety. Compared to non-conjugated hG-CSF analog, the conjugates may have lower in vitro bioactivity, longer in vivo half-life, reduced receptor-mediated clearance and/or the ability to provide a more rapid stimulation of production of white blood cells and neutrophils.

Another aspect of the present invention relates to isolated polynucleotides encoding the hG-CSF of the present invention. The polynucleotide molecule of the present invention (i.e., the polynucleotide encoding the hG-CSF analog of the present invention and the polynucleotide molecule which is complementary to such a nucleotide sequence) can be generated using standard molecular biology techniques and the sequence information provided herein, as well as sequence information known in the art. For example, the polynucleotide encoding the hG-CSF analog may be generated by site-directed mutagenesis of a polynucleotide encoding the wild-type hG-CSF. Alternatively, the polynucleotide encoding the hG-CSF analog can be prepared by standard synthetic techniques, e.g., using an automated DNA synthesizer.

The polynucleotide molecule of the invention, moreover, can comprise only a portion of the polynucleotide sequence encoding the hG-CSF analog, for example, a fragment which can be used as a probe or primer. The probe/primer typically comprises a substantially purified oligonucleotide. The oligonucleotide typically comprises a region of nucleotide sequence that hybridizes under stringent conditions to at least about 7 or 15, preferably about 25, more preferably about 50, 75, 100, 125, 150, 175, 200, 225, 250, 275, 300, 325, 350, 400 or more consecutive nucleotides of the hG-CSF analog of the invention.

Probes based on the nucleotide sequence of the hG-CSF analog of the invention can be used to detect transcripts or genomic sequences corresponding to the hG-CSF analog of the invention. In preferred embodiments, the probe comprises a label group attached thereto, e.g., the label group can be a radioisotope, a fluorescent compound, an enzyme, or an enzyme co-factor. Such probes can be used as a part of a diagnostic kit for identifying cells or tissue which expresses the hG-CSF analog.

The invention encompasses all polynucleotide molecules that encode the same proteins due to degeneracy of the genetic code.

The invention also encompasses polynucleotide molecules which are structurally different from the molecules described above (i.e., which have a slight altered sequence), but which have substantially the same properties as the molecules above (e.g., encoded amino acid sequences, or which are changed only in non-essential amino acid residues).

In another embodiment, an isolated polynucleotide molecule of the invention is at least 15, 20, 25, 30, 50, 100, 150, 200, 250, 300, 350, 400, 450, 500, 550, 600, or more nucleotides in length and hybridizes under stringent conditions to a polynucleotide molecule corresponding to a nucleotide sequence of the hG-CSF analog of the invention. Preferably, the isolated polynucleotide molecule of the invention hybridizes under stringent conditions to the sequence of the hG-CSF analog.

The skilled artisan will further appreciate that changes can be introduced by mutation into the nucleotide sequences of the hG-CSF analog of the invention, thereby leading to changes in the amino acid sequence of the encoded proteins, without altering the functional activity of these proteins. An isolated polynucleotide molecule encoding the hG-CSF analog with a mutation can be created by introducing one or more nucleotide substitutions, additions or deletions into the nucleotide sequence of the polynucleotide molecule encoding the original hG-CSF analog, such that one or more amino acid substitutions, additions or deletions are introduced into the encoded protein. Such techniques are well known in the art. Mutations can be introduced into the hG-CSF analog of the invention by standard techniques, such as site-directed mutagenesis and PCR-mediated mutagenesis.

A polynucleotide may be further modified to increase stability in vivo. Possible modifications include, but are not limited to, the addition of flanking sequences at the 5' and/or 3' ends; the use of phosphorothioate or 2O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Another aspect of the invention pertains to vectors containing a polynucleotide encoding the hG-CSF analog or a portion thereof. One type of vector is a "plasmid," which includes a circular double-stranded DNA loop into which additional DNA segments can be ligated. In the present specification, "plasmid" and "vector" can be used interchangeably as the plasmid is the most commonly used form of vector. Vectors also include expression vectors and gene delivery vectors.

The expression vectors of the invention comprise a polynucleotide encoding the hG-CSF analog or a portion thereof in a form suitable for expression of the polynucleotide in a host cell, which means that the expression vectors include one or more regulatory sequences, selected on the basis of the host cells to be used for expression, and operatively linked to the polynucleotide sequence to be expressed. It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, such as the hG-CSF analog of the present invention.

The expression vectors of the invention can be designed for expression of the hG-CSF analog in prokaryotic or eukaryotic cells. For example, hG-CSF analog can be expressed in bacterial cells such as $E.$ $coli$, insect cells (using baculovirus expression vectors), yeast cells such as $S.$ $cerevisiae$ or mammalian cells such as CHO cells. Alternatively, the expression vector can be transcribed and translated in vitro, for example using T7 promoter regulatory sequences and T7 polymerase.

The expression of proteins in prokaryotes is most often carried out in $E.$ $coli$ with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of the recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Examples of fusion expression vectors include pGEX (Pharmacia, Piscataway, N.J.), pMAL (New England Biolabs, Beverly, Mass.) and pRITS (Pharmacia, Piscataway, N.J.) which fuse glutathione S transferase (GST), maltose E binding protein, and protein A, respectively, to the target recombinant protein.

One strategy to maximize recombinant protein expression in $E.$ $coli$ is to express the protein in host bacteria with an impaired capacity to proteolytically cleave the recombinant protein. Another strategy is to alter the polynucleotide sequence of the polynucleotide to be inserted into an expression vector so that the individual codons for each amino acid are those preferentially utilized in $E.$ $coli$. Such alteration of polynucleotide sequences of the invention can be carried out by standard DNA synthesis techniques.

In another embodiment, the hG-CSF analog expression vector is a yeast expression vector. Alternatively, the hG-CSF analog of the present invention can be expressed in insect cells using baculovirus expression vectors.

In yet another embodiment, a polynucleotide of the invention is expressed in mammalian cells using a mammalian expression vector. When used in mammalian cells, the expression vector's control functions are often provided by viral regulatory elements. For example, commonly used promoters are derived from polyoma, adenovirus 2, cytomegalovirus and Simian Virus 40.

The invention further provides gene delivery vehicles for delivery of polynucleotides to cells, tissues, or a mammal for expression. For example, a polynucleotide sequence of the invention can be administered either locally or systemically in a gene delivery vehicle. These constructs can utilize viral or non-viral vector approaches in in vivo or ex vivo modality. Expression of the coding sequence can be induced using endogenous mammalian or heterologous promoters. Expression of the coding sequence in vivo can be either constituted or regulated. The invention includes gene delivery vehicles capable of expressing the contemplated polynucleotides. The gene delivery vehicle is preferably a viral vector and, more preferably, a retroviral, lentiviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, togavirus viral vector.

The gene delivery vehicles of this invention are not limited to the above-mentioned viral vectors. Other delivery methods and media may be employed such as, for example, nucleic acid expression vectors, polycationic condensed DNA linked or unlinked to killed adenovirus alone, ligand linked DNA, liposomes, eukaryotic cell delivery vehicles cells, deposition of photopolymerized hydrogel materials, handheld gene transfer particle gun, ionizing radiation, nucleic charge neutralization or fusion with cell membranes. Particle mediated gene transfer may be employed. Briefly, DNA sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose or transferrin. Naked DNA may also be employed. Uptake efficiency of naked DNA may be improved using biodegradable latex beads. The method may be improved further by treatment of the beads to increase hydrophobicity and thereby facilitate disruption of the endosome and release of the DNA into the cytoplasm.

In addition, libraries of fragments of a protein coding sequence corresponding to the hG-CSF analog of the invention can be used to generate a diverse or heterogenous population of hG-CSF analog fragments for screening and subsequent selection of functional variants of an hG-CSF analog. In one embodiment, a library of coding sequence fragments can be generated by treating a double-stranded PCR fragment of an hG-CSF analog coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, an expression library can be derived which encodes N-terminal, C-terminal and internal fragments of various sizes of the hG-CSF analog.

Several techniques are known in the art for screening gene products of combinatorial libraries made by point mutations or truncation, and for screening cDNA libraries for gene products having a selected property. The most widely used techniques, which are amenable to high-throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify hG-CSF variants (Delgrave, et al. Protein Engineering 6:327-331, 1993).

Another aspect of the invention pertains to host cells into which a polynucleotide molecule of the invention is introduced. In one embodiment, the polynucleotide molecule contains sequences which allow it to homologously recombine into a specific site of the host cell's genome. In another embodiment, the polynucleotide molecule of the invention is introduced into the host cell by a viral or a non-viral vector. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the hG-CSF analog of the invention can be expressed in bacterial cells such as K coil, insect cells, yeast or mammalian cells (such as Chinese hamster ovary cells (CHO), COS cells, Fischer 344 rat cells, HLA-B27 rat cells, HeLa cells, A549 cells, or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign polynucleotides (e.g., DNA) into a host cell, including calcium phosphate or calcium chloride co-precipitation, DEAE-dextran-mediated transfection, lipofection, or electroporation.

For stable transfection of mammalian cells, it is known that, depending upon the expression vector and transfection technique used, only a small fraction of cells may integrate the foreign DNA into their genome. In order to identify and select these integrants, a gene that encodes a selectable flag (e.g., resistance to antibiotics) is generally introduced into the host cells along with the gene of interest. Preferred selectable flags include those which confer resistance to drugs, such as G418, hygromycin and methotrexate. Polynucleotides encoding a selectable flag can be introduced into a host cell on the same vector as that encoding the hG-CSF analog of the invention or can be introduced on a separate vector. Cells stably transfected with the introduced polynucleotide can be identified by drug selection (e.g., cells that have incorporated the selectable flag gene will survive, while the other cells die).

A host cell of the invention, such as a prokaryotic or eukaryotic host cell in culture, can be used to produce (i.e., express) the hG-CSF analog of the invention. Accordingly, the invention further provides methods for producing hG-CSF analog of the invention using the host cells of the invention. In one embodiment, the method comprises culturing the host cell of invention (into which a recombinant expression vector encoding the hG-CSF analog of the invention has been introduced) in a suitable medium such that hG-CSF analog of the invention is produced. In another embodiment, the method further comprises isolating hG-CSF analog of the invention from the medium or the host cell.

One aspect of the present invention directs to methods of preventing or reducing the likelihood of implantation failure and spontaneous abortion in a recipient of FET, ICSI, GIFT or ZIFT, methods of preventing or reducing the likelihood of spontaneous abortion, and methods of treating or preventing or reducing the likelihood of preeclampsia and preterm labor described in detail below.

Methods for Preventing or Reducing the Likelihood of Implantation Failure or Spontaneous Abortion in a Recipient of FET, ICSI, GIFT or ZIFT by Administration of G-CSF In one aspect, the present invention provides methods of preventing or reducing the likelihood of embryo implantation failure, spontaneous abortion in recipients of FET, ICSI, GIFT or ZIFT by administrating to a subject in need thereof an effective amount of G-CSF.

Frozen Embryo Transfer (FET)

When excess embryos created in the process of in vitro fertilization (IVF) are not transferred to the uterus, they can be frozen for future cycles. With the current worldwide trend to try to prevent birth of multiples as a result of IVF, elective single embryo transfer becomes more prevalent. As a result, frozen embryo transfer cycles will increase in popularity. The pregnancy rate following the fresh transfer of a single embryo followed by, if necessary, the transfer of a single thawed embryo is remarkably similar to that of transferring two fresh embryos, while eliminating the risk of twins almost completely.

In a FET cycle, the uterine lining may be prepared using hormones or the transfer may be performed using a natural cycle. The embryo(s) is/are thawed and transferred to the uterus in the same process as in a fresh NF cycle. In a typical procedure, patient is monitored with ultrasound until the dominant follicle is greater than 14 mm in mean diameter, then followed with daily urine LH testing. Once ovulation is confirmed by LH surge, the thawed embryo transfer is planned. The timing of the transfer varies according to the day on which the embryos were frozen. For example, day 3 frozen embryos cycles are done with transfer on day 4-5 after the LH surge. Blastocyst FET cycles are done with transfer on day 7-8 after the LH surge. Pregnancy test is typically performed 9 to 14 days after embryo transfer, depending on the stage of embryos at FET.

In the case of hormone replacement cycle, GnRH agonist (such as Lupron) is given, either midluteal (day 21) or overlapping with a birth control pill. Down-regulation of GnRH is confirmed by ultrasound and blood tests. Estradiol valerate 2 mg twice daily (orally) is started after the period. This dose may need to be increased after monitoring of the uterine lining thickness. When the endometrium has a "good" thickness, progesterone is started (intramuscular shots, or a vaginal product). Embryo transfer is planned for 3-6 days later— depending on the stage of development of the embryos to be transferred. Estrogen and progesterone is continued in the luteal phase. Pregnancy testing is done 9-14 days after transfer—depending on the stage of development of the embryos replaced and the preferences of the fertility clinic. If pregnant, estrogen and progesterone are continued until about 10-15 weeks of pregnancy and then weaned off.

Intracytoplasmic Sperm Injection (ICSI)

ICSI is an in vitro fertilization procedure in which a single sperm is injected directly into an egg. It is a very effective method to fertilize eggs in vitro after they have been retrieved from the female partner. During an ICSI procedure, sperms are collected from the male partner by ejaculation or by surgical extraction from a testicle through a small incision. The later method of sperm retrieval is done when there is a blockage that prevents sperm from being ejaculated or when there is a problem with sperm development. To screen for possible genetic problems that could affect offspring, experts recommend that men with little or no sperm in their semen (not due to a blockage) have genetic testing before they proceed with ICSI.

Eggs are retrieved from the female partner. Typically, the female partner will get daily injections gonadotropin or follicle-stimulating hormone (FSH) to stimulate the ovaries to produce multiple eggs (superovulation) and will be closely monitored for 2 weeks before egg retrieval. After the first week, the blood estrogen levels are checked and ultrasound is used to determine whether eggs are maturing in the follicles. During the second week, the gonadotropin or FSH dosage may change based on test results and ultrasound. If follicles are fully developed, the female partner is given a human chorionic gonadotropin (hCG) injection to stimulate the follicles to mature. The mature eggs are collected 34 to 36 hours later using laparoscopy or needle aspiration guided by ultrasound through the abdomen to the ovaries.

The injection is done under a microscope using multiple micromanipulation devices (micromanipulator, microinjectors and micropipettes). A holding pipette (on the left of picture) stabilizes the mature oocyte with gentle suction applied by a microinjector. From the opposite side a thin, hollow glass micropipette is used to collect a single sperm, having immobilized it by cutting its tail with the point of the micropipette. The micropipette is pierced through the oolemma and into the inner part of the oocyte (cytoplasm). The sperm is then released into the oocyte. After the procedure, the oocyte will be placed into cell culture and checked on the following day for signs of fertilization.

After culturing in the laboratory overnight, eggs are checked for evidence of fertilization. The sperm injection will usually result in normal fertilization in approximately 70-85% of eggs injected with viable sperms. After incubation, the eggs that have been successfully fertilized (zygotes) or have had 3 to 5 days to further develop (zygotes or blastocysts) are selected. Two to four are placed in the uterus using a thin flexible tube (catheter) that is inserted through the cervix. The remaining embryos may be frozen (cryopreserved) for future attempts.

Gamete Intra-Fallopian Transfer (GIFT)

GIFT is an early, and very simple technique devised in the 1980s to achieve pregnancies in most couples who have not been able to conceive using conventional treatments for infertility (despite having good sperm and normal fallopian tubes). GIFT is the only assisted reproductive technology (ART) approach that is completely acceptable to the Roman Catholic Church. In a GIFT procedure, a semen sample from the male partner is obtained. The sperm is washed and prepared for loading into a catheter into which several of the female partner's eggs will be placed. The eggs are obtained by transvaginal needle aspiration (no surgical incision) via an ultrasound guide. The eggs are placed in a laboratory dish and observed under a microscope and their stage of maturity noted. The best eggs are loaded into the same catheter with the sperms. The eggs and sperm are then released into the fallopian tube. The number of eggs returned to the patient depends on the female's age and egg quality. This procedure can be performed surgically either through laparoscopy or a small, one-inch "mini-lap" incision in the lower abdomen, under general anesthesia.

With GIFT, fertilization occurs inside the woman's body (not outside), and mimics the way a normally fertilized egg would begin its journey to the uterus for implantation. One of GIFT's major advantages over IVF is that the technique relies to a far greater degree on the body's natural processes and timetable to produce pregnancy, and is acceptable to those religious groups which avoid the more embryo invasive technologies.

Zygote Intra-Fallopian Transfer (ZIFT)

ZIFT is similar to the GIFT procedure, except that the eggs are fertilized in vitro first and the fertilized eggs are then placed into the woman's fallopian tubes. ZIFT differs from GIFT in that fertilization takes place in a laboratory dish instead of the fallopian tube. Moreover, it differs from IVF in that the fertilized egg is transferred to the fallopian tube instead of to the uterus. Thus, this advanced option offers the best of both IVF and GIFT—documentation of fertilization in vitro; and higher pregnancy rates because of tubal transfer.

It typically takes about 5 weeks to complete a cycle of ZIFT. First, the woman must take a fertility medication to stimulate egg production in the ovaries. The doctor will monitor the growth of the ovarian follicles, and once they are mature, the woman will be injected with human chorionic gonadotropins (hCG). The eggs will be harvested approximately 36 hours later, usually by transvaginal ovum retrieval. After fertilization in the laboratory the resulting early embryos or zygotes are placed into the woman's fallopian tubes using a laparoscope.

While not intending to be bound by any particular theory of operation, it is believed that a significant percentage of implantation failure and spontaneous abortion in recipients of FET, ICSI, GIFT and ZIFT is caused by or associated with inappropriate immune responses in these recipients. In particular, it is believed that subjects at risk for embryo implantation failure or spontaneous abortion present with an overproduction of T-helper 1 (Th1) cytokines and underproduction of T-helper 2 (Th2) cytokines. Positive correlations in human and animal models have been demonstrated, (see, Kwak-Kim et al., 2003, Human Reproduction 18:767-73, Krishnan et al., 1996, J. Immunol. 156:653-62) but remain controversial (see, Chaouat et al., 2003, J. Reproductive Immunol. 59:205-17). The Th1 cytokine associated with overproduction can be interferon-$\gamma$ (INF-$\gamma$). The Th2 cytokines associated with underproduction can be interleukins 10 and 4 (IL-10 and IL-4).

To prevent or reduce the likelihood or risk of implantation failure or spontaneous abortion, the G-CSF is typically administered before the embryo/zygote/gamete transfer or sperm injection. The administration is continued until implantation of the embryo to the uterine wall is achieved, until the risk of failed implantation is reduced or eliminated, or according to the judgment of a practitioner of skill in the art. In other embodiments, the G-CSF is administered to a pregnant subject. The dose can be administered to the subject daily until the risk of implantation failure or spontaneous abortion is reduced or eliminated and as long as no symptoms of toxicity are presented. In certain embodiments, the G-CSF can be administered at any time during the first or second trimester of pregnancy. In certain embodiments, the dose is administered daily through the second trimester of pregnancy. In further embodiments, the dose is administered daily through the 20th week of pregnancy. In preferred embodiments, the G-CSF is administered during the first 20 weeks of pregnancy. In particular embodiments, the dose is administered daily for four, three, two or one week during the first or second trimester of pregnancy. In particular embodiments, the dose is administered for five consecutive days during the first or second trimester of pregnancy. For example, the five consecutive days can be in the first or second week of pregnancy.

In certain embodiments, the administration is continued until pregnancy is confirmed. In certain embodiments, G-CSF is administered daily for 1-35 consecutive days. In other embodiments, G-CSF is administered daily until the end of first trimester. In certain embodiments the administration is started before the time of controlled ovarian hyperstimulation or about the time of controlled ovarian hyperstimulation, and continued daily until about 3 days, about 5 days, about 7 days, about 10 days, about 12 days, about 14 days, about 30 days, about 45 days, or about 60 days after embryo/zygote/gamete transfer or sperm injection into the subject's vagina, cervix, uterus, or fallopian tubes. In certain embodiments, the administration is started about 14 days, 7 days, 5 days, 3 days, and 1 day before the embryo/zygote/gamete transfer or sperm injection. In another embodiment, the administration is started about the time of controlled ovarian hyperstimulation and continued daily until about the end of the first trimester. In another embodiment, the dose is administered for five consecutive days about the time of embryo/zygote/gamete transfer or sperm injection and continued daily until about 3 days, about 5 days, about 7 days, about 10 days, about 12 days, about 14 days, about 30 days, about 45 days, or about 60 days after the embryo/zygote/gamete transfer or sperm injection: In certain embodiments, the administration is continued daily until the subject presents a normal Th1 immune response or a normal Th2 immune response or both, according to the judgment of a practitioner of skill in the art.

In certain embodiments, the recipient is a subject that has failed one or more assisted reproduction technology (ART) procedures. In further embodiments, the recipient is a subject undergoing her first ART procedure. The subject can be any mammalian subject at risk for implantation failure or spontaneous abortion. In particularly preferred embodiments, the subject is a human female. In further embodiments, the recipient can also be in any other population at risk for failed embryo implantation or spontaneous abortion as determined by a practitioner of skill in the art. In another embodiment, the recipient has had one or more previous spontaneous abortions. In further embodiments, the subject has previously had two or more spontaneous abortions. In other embodiments, the subject has had recurrent spontaneous abortions, i.e., three or more spontaneous abortions. In another embodiment, the recipient has unusually high Th1 immune responses or unusually low Th2 immune responses.

In certain embodiments, the G-CSF is administered to the subject prior to embryo/zygote/gamete transfer or sperm injection. For instance, the G-CSF is administered to a subject that is planning or attempting to become pregnant via FET, ICSI, GIFT or ZIFT. Thus, the G-CSF can be administered to the mother-to-be during the controlled ovarian hyperstimulation procedure or prior to the embryo/zygote/gamete transfer or sperm injection if no controlled ovarian hyperstimulation procedure is used. The G-CSF can be administered at any time during the FET, ICSI, GIFT or ZIFT process.

In certain embodiments, the retrieved oocytes or embryos are maintained and cultured in medium containing G-CSF prior to their transfer to the uterus of the recipient.

Methods for Treating, Preventing or Reducing Risk of Preeclampsia or Preterm Labor in a Recipient of FET, ICSI, GIFT or ZIFT with G-CSF In a further aspect, the present invention provides methods of treating, preventing or reducing the risk of preeclampsia or preterm labor by administering to a recipient of FET, ICSI, GIFT or ZIFT an effective amount of granulocyte colony stimulating factor.

While not intending to be bound by any particular theory of operation, it is believed that preeclampsia and preterm labor is caused or associated with inappropriate immune responses in a pregnant subject. In particular, it is believed that subjects at risk for preeclampsia or preterm labor present inappropriate immune cytokines associated with a T-helper 1 (Th1) immune response known to those of skill in the art. In contrast, subjects that have healthy pregnancies typically present immune cytokines associated with a T-helper 2 immune response. It is believed that administration of G-CSF can reduce the inappropriate Th1 response and/or increase a Th2 immune response in a subject. This invention is thus based, in part, on the discovery that administration of G-CSF can shift a subject's immune response towards a healthy Th2 response during pregnancy and thereby treat or prevent preeclampsia or preterm labor.

In the methods of treatment, G-CSF is administered to a recipient of FET, ICSI, GIFT or ZIFT presenting one or more signs or symptoms of preeclampsia or preterm labor. The recipient can be any recipient that presents any of the signs or symptoms of preeclampsia during pregnancy such as hypertension, swelling or edema and excessive protein in the urine. For example, the recipient can be any recipient that develops hypertension with albuminuria or edema between the 20th week of pregnancy and the end of the 1st week postpartum. Particular recipient include pregnant females who develop a blood pressure of 140/90 mm Hg, edema of the face or hands or albuminuria of $\geqq 1+$ or whose blood pressure rises by 30 mm Hg systolic or 15 mm. Hg diastolic (even if less than 140/190 mm Hg) between the 20th week of pregnancy and the end of the 1st week postpartum. Particularly preferred subjects are human females.

In the methods of treatment, the G-CSF is typically administered until the signs or symptoms of preeclampsia or preterm labor are alleviated or reduced as long as the therapeutic benefit outweighs the risk of adverse events according to the judgment of a practitioner of skill in the art. The dosing can continue as long as the recipient displays no toxic effects of the administration according to the judgment of a practitioner of in the art. In certain embodiments, the treatment is continued until the recipient presents a normal Th1 immune response for a pregnant recipient or a normal Th2 response for a pregnant recipient, or both, according to the judgment of a practitioner of skill in the art.

In the methods of prevention, G-CSF is administered to a recipient at risk for developing preeclampsia or preterm labor. Recipients at risk include recipients carrying multiple babies, recipients younger than age 20 and recipients older than age 40. Further recipients include those pregnant for the first time (primigravida), recipients with preexisting hypertension and subjects with preexisting vascular disease. Other recipients at risk include those with unusually high Th1 immune responses or unusually low Th2 immune responses. In particularly preferred embodiments, the recipient is a human female.

In the methods of prevention, G-CSF is administered as long as the recipient is at risk for preeclampsia and as long as the therapeutic benefit outweighs the risk of adverse events and also, so long as no toxicity is observed according to the judgment of a practitioner of skill in the art. In certain embodiments, G-CSF is administered for the duration of the pregnancy. In particular embodiments, administration is provided in the 2nd and 3rd trimester of pregnancy. In further embodiments, administration is continued after delivery for about one, about two, about three, about four, about five, about six, about seven or about eight weeks post partum. In certain embodiments, the treatment is continued until the recipient presents a normal Th1 immune response for a pregnant recipient or a normal Th2 immune response for a pregnant recipient, or both, according to the judgment of a practitioner of skill in the art.

The G-CSF can be administered according to any method of administration known to those of skill in the art. Preferred methods of administration include subcutaneous administration. Other effective modes of administration are described in detail in the sections below.

Methods for Preventing or Reducing the Likelihood of Implantation Failure or Spontaneous Abortion in a Recipient of FET, ICSI, GIFT or ZIFT by Administration of hG-CSF Analog In one aspect, the present invention provides methods of preventing or reducing the likelihood of embryo implantation failure and spontaneous abortion in recipients of FET, ICSI, GIFT or ZIFT by administrating to a subject in need thereof an effective amount of a hG-CSF analog.

To prevent or reduce the likelihood of implantation failure, the hG-CSF analog is typically administered before the embryo/zygote/gamete transfer or sperm injection. The administration is continued until implantation of the embryo to the uterine wall is achieved, until the risk of failed implantation is reduced or eliminated, or according to the judgment of a practitioner of skill in the art.

In certain embodiments, the administration is continued until pregnancy is confirmed. In certain embodiments, hG-CSF analog is administered daily for 1-35 consecutive days. In other embodiments, hG-CSF analog is administered daily until the end of first trimester. In certain embodiments the administration is started before the time of controlled ovarian hyperstimulation or about the time of controlled ovarian hyperstimulation, and continued daily until about 3 days, about 5 days, about 7 days, about 10 days, about 12 days, about 14 days, about 30 days, about 45 days, or about 60 days after embryo/zygote/gamete transfer or sperm injection into the subject's vagina, cervix, uterus, or fallopian tubes. In certain embodiments, the administration is started about 14 days, 7 days, 5 days, 3 days, and 1 day before the embryo/zygote/gamete transfer or sperm injection. In another embodiment, the administration is started about the time of controlled ovarian hyperstimulation and continued daily until about the end of the first trimester. In another embodiment, the dose is administered for five consecutive days about the time of embryo/zygote/gamete transfer or sperm injection and continued daily until about 3 days, about 5 days, about 7 days, about 10 days, about 12 days, about 14 days, about 30 days, about 45 days, or about 60 days after the embryo/zygote/gamete transfer or sperm injection. In certain embodiments, the administration is continued daily until the subject presents a normal Th1 immune response or a normal Th2 immune response or both, according to the judgment of a practitioner of skill in the art.

In certain embodiments, the recipient is a recipient that has failed one or more assisted reproduction technology (ART) procedures. In farther embodiments, the recipient is a recipient undergoing her first ART procedure. In further embodiments, the recipient can also be in any other population at risk for failed embryo implantation or spontaneous abortion as determined by a practitioner of skill in the art. In another embodiment, the recipient has had one or more previous spontaneous abortions. Other recipients at risk include those with unusually high Th1 immune responses or unusually low Th2 immune responses.

In certain embodiments, the hG-CSF analog is administered to the subject prior to embryo/zygote/gamete transfer or sperm injection. For instance, the hG-CSF analog is administered to a subject that is planning or attempting to become pregnant via FET, ICSI, GIFT or ZIFT. Thus, the hG-CSF analog can be administered to the mother-to-be during the controlled ovarian hyperstimulation procedure or prior to the embryo/zygote/gamete transfer or sperm injection if no controlled ovarian hyperstimulation procedure is used. The hG-CSF analog can be administered at any time during the FET, ICSI, GIFT or ZIFT process.

In certain embodiments, the retrieved oocytes or embryos are maintained and cultured in medium containing hG-CSF analog prior to their transfer to the uterus of the recipient.

Methods for Treating, Preventing or Reducing the Likelihood of Preeclampsia or Preterm Labor in a Recipient of FET, ICSI, GIFT or ZIFT with hG-CSF Analog In a further aspect, the present invention provides methods of treating, preventing or reducing the risk of preeclampsia or preterm labor in a recipient of FET, ICSI, GIFT or ZIFT by administering to the recipient an effective amount of granulocyte colony stimulating factor.

In the methods of treatment, hG-CSF analog is administered to a recipient of FET, ICSI, GIFT or ZIFT presenting one or more signs or symptoms of preeclampsia or preterm labor. The recipient can be any recipient that presents any of the signs or symptoms of preeclampsia during pregnancy such as hypertension, swelling or edema and excessive protein in the urine. For example, the recipient can be any recipient that develops hypertension with albuminuria or edema between the 20th week of pregnancy and the end of the 1st week postpartum. Particular recipients include pregnant females who develop a blood pressure of 140/90 mm Hg, edema of the face or hands or albuminuria of $\geq 1+$ or whose blood pressure rises by 30 mm Hg systolic or 15 mm Hg diastolic (even if less than 140/190 mm Hg) between the 20th week of pregnancy and the end of the 1st week postpartum. Particularly preferred subjects are human females.

In the methods of treatment, the hG-CSF analog is typically administered until the signs or symptoms of preeclampsia or preterm labor are alleviated or reduced as long as the therapeutic benefit outweighs the risk of adverse events according to the judgment of a practitioner of skill in the art. The dosing can continue as long as the recipient displays no toxic effects of the administration according to the judgment of a practitioner of in the art. In certain embodiments, the treatment is continued until the recipient presents a normal Th1 immune response for a pregnant recipient or a normal Th2 response for a pregnant recipient, or both, according to the judgment of a practitioner of skill in the art.

In the methods of prevention, hG-CSF analog is administered to a recipient of FET, ICSI, GIFT or ZIFT who is at risk for developing preeclampsia or preterm labor. The recipient can be any mammalian subject at risk for preeclampsia or preterm labor. recipients at risk include recipients carrying multiple babies, recipients younger than age 20 and recipients older than age 40. Further recipients include those pregnant for the first time (primigravida), recipients with preexisting hypertension and recipients with preexisting vascular disease. Other recipients at risk include those with unusually high Th1 immune responses or unusually low Th2 immune responses. In particularly preferred embodiments, the recipient is a human female.

In the methods of prevention, hG-CSF analog is administered as long as the recipient is at risk for preeclampsia and as long as the therapeutic benefit outweighs the risk of adverse events and also, so long as no toxicity is observed according to the judgment of a practitioner of skill in the art. In certain embodiments, hG-CSF analog is administered for the duration of the pregnancy. In particular embodiments, administration is provided in the 2nd and 3rd trimester of pregnancy. In further embodiments, administration is continued after delivery for about one, about two, about three, about four, about five, about six, about seven or about eight weeks post partum. In certain embodiments, the treatment is continued until the recipient presents a normal Th1 immune response for a pregnant recipient or a normal Th2 immune response for a pregnant recipient, or both, according to the judgment of a practitioner of skill in the art.

The hG-CSF analog can be administered according to any method of administration known to those of skill in the art. Preferred methods of administration include subcutaneous administration. Other effective modes of administration are described in detail in the sections below.

G-CSF and Formulation

As described in detail above, the present invention provides methods of administering an effective amount of G-CSF or hG-CSF analog to prevent or reduce the likelihood of spontaneous abortion, implantation failure, preeclampsia or preterm labor in recipients of FET, ICSI, GIFT or ZIFT.

The G-CSF administered in the methods of the invention can be any G-CSF known to one of skill in the art without limitation. Thus, a range of modifications can be made to the wild-type G-CSF molecules so long as the known immune system modulating activity of the G-CSF is maintained, including hG-CSF analog. There are a number of assays that can be used to ensure that any one modified G-CSF retains the desired immune system modulating activity. Plural types of G-CSF or hG-CSF analog molecules can be administered in the practice of the instant invention. The plural G-CSF or hG-CSF analog molecules can be administered concurrently, consecutively, or sequentially. In certain embodiments, the G-CSF can be any G-CSF or any derivative, variant, mimetic, chemically modified version or hybrid thereof, as described in U.S. Pat. Nos. 5,399,345; 5,416,195; 5,981,551; 6,166,183 and 6,261,550, the contents of which are hereby incorporated by reference in their entireties. In certain other embodiments, the G-CSF can be a hG-CSF analog. In further embodiments, the G-CSF or hG-CSF analog can be administered in the form of a nucleotide sequence encoding G-CSF or hG-CSF analog, or expression vectors encoding G-CSF described in U.S. Pat. No. 5,422,248, the content of which is hereby incorporated by reference in its entirety. The G-CSF or hG-CSF analog can be formulated according to any formulation for administration known to those of skill in the art.

In certain embodiments, the G-CSF is a commercially available G-CSF available as a pharmaceutical composition, suitable for administration to an animal, including a human. Such commercially available pharmaceutical compositions can be, for example, filgrastim (Neupogen® (Amgen), Tevagrastim® (Teva), Biograstim® (CT Arzneimittel), Ratiograstim® (Ratiopharm GmbH), Zarzio® (Sandoz GmbH), Filgrastim Hexal® (Hexal AG), pegfilgrastim (Neulasta®, Amgen), nartograstim (Neu-Up®, Kyowwa) or lenograstim (Neutrogin®, Granocyte®, Chugai).

Filgrastim, nartograstim, and lenograstim are useful for promoting neutrophil proliferation and are generally administered to individuals in need to increased neutrophils, for example, patients undergoing chemotherapy. Filgrastim, nartograstim, and lenograstim are indicated for myelosuppressive chemotherapy, bone marrow transplant, peripheral blood progenitor cell collection and severe chronic neutropenia. Off label uses include treatment of neutropenia in AIDS patients, aplastic anemia, hairy cell leukemia, myelodysplasia, drug-induced and congenital agranulocytosis and alloimmune neonatalneutropenia.

The usual treatment of neutropenia associated with myelosuppression is 5 mcg/kg/day, once daily either by bolus subcutaneously or short (15-30 minute) intravenous infusion or by continuous subcutaneous or intravenous infusion. Administration is once daily starting no earlier than 24 hours after chemotherapy and continues for 14 days or until the individual's absolute neutrophil count is 10,000/mm3. For patients undergoing bone marrow transplant, the usual dose is 10 mcg/kg/day administered as an intravenous infusion over 4-24 hours or as a continuous 24 hour subcutaneous infusion. The first dose is generally administered at least 24 hours after chemotherapy and at least 24 hours after bone marrow infusion. During recovery, the dose is adjusted according to the patient's absolute neutrophil count. Filgrastim dosing for peripheral blood progenitor cells generally begins at 10

μg/kg/day subcutaneously either as a bolus or continuous infusion. It is recommended that filgrastim be given for at least four days before leukapheresis and continued until the last leukapheresis procedure. Doses of filgrastim for congenital neutropenia are 5 mcg/kg subcutaneously twice daily while idiopathic or cyclic neutropenia is generally treated with a dose of 5 mcg/kg subcutaneously once daily.

Pegfilgrastim is a monomethoxypolyethylene glycol conjugate of filgrastim. The pharmaceutical composition is commercially available as preservative free solutions of 10 mg/ml pegfilgratim in prefilled single-dose syringes. Pegfilgrastim is indicated to decrease infections in patients with febrile neutropenia undergoing myelosuppressive chemotherapy. Recommended dosing is a single 6 mg subcutaneous injection administered once per chemotherapy cycle.

In the above-described methods, G-CSF is administered in an effective amount, i.e., an amount effective to reduce or eliminate the risk of embryo implantation failure or spontaneous abortion, preeclampsia or preterm labor in recipients of FET, ICSI, GIFT or ZIFT. The effective amount can be determined by the skilled practitioner guided by the description herein and the knowledge in the art. In preferred embodiments, the amount can be any amount of G-CSF that reduces the Th1 response of the subject. In further embodiments, the amount can be any amount sufficient to increase or initiate a Th2 response in the subject. Assays to determine Th1 and Th2 responses in the subject are well known to those of skill in the art (See e.g., Schust and Hill, 1996, J. Soc. Gynecol Investig. 3:259-61, Xing et al., 2001, Chin. Med. J. 114:921-4, Raghupathy et al., 1999, Cell Immunol. 196:122-30, Mauri et al., 1996, J. Immunol. 26:1511-8, Doncorli et al., 1997, Eur. J. Imm. 27:1451-8, Raziuddin, 1998, J. Rheumatol 25:329-33, Moverare et al., 2000, Allergy 55:171-5). In particular embodiments, G-CSF is administered at doses of about 0.1 mcg/kg/day to 600 mcg/kg/day, 0.5 mcg/kg/day to 300 mcg/kg/day, 1 mcg/kg/day to 100 mcg/kg/day, 1 mcg/kg/day to 50 mcg/kg/day, 1 mcg/kg/day to 20 mcg/kg/day, 1 mcg/kg/day to 10 mcg/kg/day, 1 mcg/kg/day to 2 mcg/kg/day; and about 1.67 mcg/kg/day. In another embodiment, at least 0.01 mg, at least 0.02 mg, at least 0.05 mg at least 0.1 mg, at least 0.2 mg, at least 0.5 mg, at least 1 mg, at least 2 mg, at least 5 mg, at least 10 mg, at least 25 mg, at least 50 mg, at least 75 mg, at least 100 mg, at least 125 mg, at least 150 mg, at least 175 mg, at least 200 mg, at least 300 mg, at least 600 mg or more is administered daily.

In other embodiments, hG-CSF analog is administered in an effective amount, i.e., an amount effective to reduce or eliminate the risk of implantation failure, spontaneous abortion, preeclampsia or preterm labor in recipients of FET, ICSI, GIFT or ZIFT. The amount can be determined by the skilled practitioner guided by the description herein and the knowledge in the art. In preferred embodiments, the amount can be any amount of hG-CSF analog that reduces the Th1 response of the subject. In further embodiments, the amount can be any amount sufficient to increase or initiate a Th2 response in the subject. Assays to determine Th1 and Th2 responses in the subject are well known to those of skill in the art (See e.g., Schust and Hill, 1996, J. Soc. Gynecol Investig. 3:259-61, Xing et al., 2001, Chin. Med. J. 114:921-4, Raghupathy et al., 1999, Cell Immunol. 196:122-30, Mauri et al., 1996, J. Immunol. 26:1511-8, Doncorli et al., 1997, Eur. J. Imm. 27:1451-8, Raziuddin, 1998, J. Rheumatol 25:329-33, Moverare et al., 2000, Allergy 55:171-5). In particular embodiments, hG-CSF analog is administered at doses of about 0.1 mcg/kg/day to 600 mcg/kg/day, 0.5 mcg/kg/day to 300 mcg/kg/day, 1 mcg/kg/day to 100 mcg/kg/day, 1 mcg/kg/day to 50 mcg/kg/day, 1 mcg/kg/day to 20 mcg/kg/day, 1 mcg/kg/day to 10 mcg/kg/day, 1 mcg/kg/day to 2 mcg/kg/day; and about 1.67 mcg/kg/day. In another embodiment, at least 0.01 mg, at least 0.02 mg, at least 0.05 mg at least 0.1 mg, at least 0.2 mg, at least 0.5 mg, at least 1 mg, at least 2 mg, at least 5 mg, at least 10 mg, at least 25 mg, at least 50 mg, at least 75 mg, at least 100 mg, at least 125 mg, at least 150 mg, at least 175 mg, at least 200 mg, at least 300 mg, at least 600 mg or more is administered daily.

In certain embodiments described above, the present invention provides methods of administering to a subject in need thereof an effective amount of G-CSF or hG-CSF analog as a monotherapy. In other embodiments, the present invention provides methods of administering to a subject an effective amount of G-CSF or hG-CSF analog in combination with at least one additive or other active agent. Additives or active agents include cytokines that suppress Th1 immune response, cytokines that enhance Th2 immune response, and non-myeloablative immunosuppressive agents. Additives or other active compounds can be drugs currently used to treat the conditions of interest, such as immunoglobulin or corticosteroid treatment. Additives may also include cytokines that support successful pregnancy outcome through non-immunologic mechanisms such as stimulation of trophoblast cell proliferation, inhibition of trophoblast cell apoptosis, stimulation of trophoblasat invasion, or stimulation of angiogenesis. Additives may also include anti-inflammatory agents, and inhibitors of pro-inflammatory cytokines.

Examples of additives include, but are not limited to interferon alpha, interferon beta, macrophage colony stimulating factor (M-CSF), granulocyte macrophage colony stimulating factor (GM-CSF), leukemia inhibitory factor (LIF), transforming growth factor beta (TGF-beta), interleukin-1 (IL-1), IL-3, IL-4, IL-6, IL-7, IL-8, IL-9, IL-10, IL-11, IL-13, IL-14, IL-15, IL-19, IL-20, IL-21, IL-22, IL-24, IL-25, IL-26, IL-27, IL-28, IL-29, IL-30, IL-31, IL-32, IL-33, and IL-35.

In certain embodiments, additives may include inhibitors of pro-inflammatory cytokines such as, but not limited to, anti-TNF-alpha, pentoxifyllin, anti-VEGF, anti-CD28, anti-CD80, anti-CD86, anti-CD40L, and the like.

Other additives that may be used with a G-CSF or hG-CSF analog include anti-inflammatory agents. The anti-inflammatory agent can be one that reduces leukocyte populations or inhibits leukocyte function. Other anti-inflammatory agents can be used as well. For example, vitamin D3 (1,25-dihydroxycholecalciferol) and analogs thereof can be used. In another example, corticosteroids such as prednisone or methylprednisolone can be used.

Other additives that may be used with a G-CSF or hG-CSF analog are those currently used to treat recurrent spontaneous abortion, miscarriage, implantation failure, preeclampsia or preterm labor, such as intravenous Ig and heparin.

The additive can be another CSF, erythropoietin or stem cell factor. The CSF can be G-CSF, GM-CSF or macrophage CSF.

The G-CSF or hG-CSF analog can be administered according to any method of administration known to those of skill in the art. Preferred methods of administration include subcutaneous administration, parenteral administration, enteral administration, topical administration. G-CSF or hG-CSF analog may also be administered by inhalation. In the compositions administered, the G-CSF or hG-CSF analog can be formulated in any manner known to those of skill in the art for formulating and administering effective amounts of G-CSF or hG-CSF analog.

Filgrastim or non-glycosylated G-CSF is available as a preservative-free pharmaceutical composition comprising 300 mcg/ml and 480 mcg/ml vials or 300 mcg/0.5 ml and 480 mcg/0.5 ml self-injectors. The composition can be administered subcutaneously without further admixture. Intravenous preparations require dilution with proper diluent, such as 5% dextrose, diluted to a final concentration of filgrastim of 5 to 15 mcg/ml. Saline is not recommended as a diluent due to product precipitation. Mixture with albumin is recommended to prevent adsorption to plastic or glass materials during preparation and infusion. The final concentration of human albumin should be 2 mg/ml. It is highly recommended that filgrastim be refrigerated at 2° to 8° C.

The presently available pharmaceutical composition contains a small amount of acetate, Tween 80, sodium, and sorbitol. These excipients are used to achieve and maintain characteristics that are physiologically acceptable to the body and pharmaceutically practical. Such characteristics include tonicity, osmoticity, osmolality, osmolarity, viscosity and shelf life. Aqueous pharmaceutical compositions of G-CSF with increased serum half life have been described, for example, in U.S. Pat. No. 5,919,757, incorporated herein by reference in its entirety.

The pharmaceutical compositions can comprise the G-CSF or hG-CSF analog in a salt form. For example, because proteins can comprise acidic and/or basic termini side chains, the proteins can be included in the pharmaceutical compositions in either the form of free acids or bases, or in the form of pharmaceutically acceptable salts. Pharmaceutically acceptable salts can include, suitable acids which are capable of forming salts with the proteins of the present invention including, for example, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, cinnamic acid, anthranilic acid, citric acid, naphthalene sulfonic acid, sulfanilic acid and the like. Suitable bases capable of forming salts with the subject proteins can include, for example, inorganic bases such as sodium hydroxide, ammonium hydroxide, potassium hydroxide and the like; and organic bases such as mono-, di- and tri-alkyl amines (for example, triethyl amine, diisopropyl amine, methyl amine, dimethyl amine and the like) and optionally substituted ethanolamines (for example, ethanolamine, diethanolamine and the like).

Although commercially available G-CSF is currently administered subcutaneously or intravenously, any method of administration that provides a therapeutically effective amount of G-CSF or hG-CSF analog can be used in the methods of the invention. In one aspect, G-CSF or hG-CSF analog can be in a variety of forms suitable for any route of administration, including, but not limited to, parenteral, enteral, topical or inhalation.

Parenteral administration refers to any route of administration that is not through the alimentary canal, including, but not limited to, injectable administration, i.e., intravenous, intramuscular and the like as described below. Enteral administration refers to any route of administration which is oral, including, but not limited to, tablets, capsules, oral solutions, suspensions, sprays and the like, as described below. For purposes of this invention, enteral administration also refers to rectal and vaginal routes of administration. Topical administration refers to any route of administration through the skin, including, but not limited to, creams, ointments, gels and transdermal patches, as described below (see also, Pharmaceutical Sciences, 18th Edition (Gennaro et al., eds., Mack Printing Company, Easton, Pa., 1990).

Parenteral pharmaceutical compositions of the present invention can be administered by injection, for example, into a vein (intravenously), an artery (intraarterially), a muscle (intramuscularly) or under the skin (intradermally or subcutaneously) or in a depot composition.

Injectable pharmaceutical compositions can be sterile suspensions, solutions or emulsions of the G-CSF or hG-CSF analog in aqueous or oily vehicles. The compositions can also comprise formulating agents or excipients, such as suspending, stabilizing and/or dispersing agents. The formulations for injection can be presented in unit dosage form, in ampules or in multidose containers, and can comprise added preservatives. In certain embodiments, the pharmaceutical compositions contain buffers such as citrate, acetate, phosphate, tris (hydroxymethyl)amino methane or THAM (tromethamine).

Depot or sustained release pharmaceutical compositions can be used in the methods of the invention. For example, continuous release of G-CSF or hG-CSF analog can be achieved by the conjugation of the G-CSF or hG-CSF analog with a water soluble polymer as described in U.S. Pat. No. 5,320,840. G-CSF may be contained in an inert matrix or device for slow release after implantation of the matrix or device.

Injectable compositions can be pharmaceutically appropriate compositions for any route of injectable administration, including, but not limited to, intravenous, intrarterial, intracoronary, pericardial, perivascular, intramuscular, subdermal, subcutaneous and intraarticular.

Alternatively, the injectable pharmaceutical composition can be provided in powder form for reconstitution with a suitable vehicle, including but not limited to sterile pyrogen free water, buffer, dextrose solution, etc., before use. To this end, the G-CSF or hG-CSF analog can be lyophilized as appropriate. The pharmaceutical compositions can be supplied in unit dosage forms and reconstituted prior to use in vivo.

For prolonged delivery, the pharmaceutical composition can be provided as a depot preparation, for administration by implantation; e.g., subcutaneous, intradermal, or intramuscular injection. Thus, for example, the pharmaceutical composition can be formulated with suitable polymeric or hydrophobic materials as an emulsion in an acceptable oil or ion exchange resins, or as sparingly soluble derivatives; as a sparingly soluble salt form of the G-CSF or hG-CSF analog, or derivative, mimetic or variant thereof. The G-CSF or hG-CSF analog can be present in an inert matrix or device for implantation to achieve prolonged release.

Alternatively, transdermal delivery systems manufactured as an adhesive disc or patch that slowly releases the active ingredient for percutaneous absorption can be used. To this end, permeation enhancers can be used to facilitate penetration of the G-CSF or hG-CSF analog. A particular benefit may be achieved by incorporating the G-CSF or hG-CSF analog into a transdermal patch.

For oral administration, the pharmaceutical formulations can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art (see, Remington's Pharmaceutical Sciences, 18th edition (Gennaro et al., eds.) Mack Printing Company, Pennsylvania, 1990).

Liquid pharmaceutical compositions for oral administration can take the form of, for example, solutions, syrups or suspensions, or they can be a dry product for constitution with water or other suitable vehicle before use. Such liquid pharmaceutical compositions can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid).

The pharmaceutical compositions can also comprise buffer salts, flavoring, coloring and sweetening agents as appropriate. Pharmaceutical compositions for oral administration can be suitably prepared to provide controlled release of the G-CSF or hG-CSF analog.

Enteral pharmaceutical compositions can be suitable for buccal administration, for example, in the form of tablets, troches or lozenges. For rectal and vaginal routes of administration, the G-CSF or hG-CSF analog can be prepared as solutions (e.g. for retention enemas), suppositories or ointments. Enteral pharmaceutical compositions can be suitable for admixture in feeding mixtures, such as, for mixture with total parenteral nutrition (TPN) mixtures or for delivery by a feeding tube (see, Dudrick et al., 1998, Surg. Technol. Int. VII:174-184; Mohandas et al., 2003, Natl. Med. J. India 16(1):29-33; Bueno et al., 2003, Gastroint. Endosc. 57(4): 536-40; Shike et al., 1996, Gastroint. Endosc. 44(5):536-40).

For administration by inhalation, the G-CSF or hG-CSF analog can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of e.g., gelatin for use in an inhaler or insufflator can be formulated comprising a powder mix of the compound and a suitable powder base such as lactose or starch. Inhaled pharmaceutical compositions can be those, for example, described in U.S. Pat. Nos. 5,284,656 and 6,565,841, incorporated herein by reference in their entirety.

The compositions can, if desired, be presented in a pack or dispenser device that can comprise one or more unit dosage forms comprising the G-CSF or hG-CSF analog. The pack can, for example, comprise metal or plastic foil, such as a blister pack. The pack or dispenser device can be accompanied by instructions for administration.

The pharmaceutical compositions can be for a single, one time use or can contain antimicrobial excipients, rendering the composition suitable for multiple, extended use with greater shelf stability; for example, a multi-use bottle. In another embodiment, the pharmaceutical composition of interest can be in unit dose or unit-of-use packages. As known in the art, a unit dose is targeted for a single use. The unit dose form can be in a vial, which can contain a solution or a desiccated form for reconstitution, a pre-filled syringe, a transdermal patch and the like.

As is known to those of skill in the art, a unit-of-use package is a convenient prescription size, patient ready unit labeled for distribution by health care providers. The package contains as much active ingredient as necessary for a typical treatment regimen.

The pharmaceutical composition can be labeled and have accompanying labeling to identify the composition contained therein and other information useful to health care providers and end users. The information can include instructions for use, dose, dosing interval, duration, indication, side effects and other contraindications, warnings, precautions, storage recommendations and the like.

Various embodiments of the pharmaceutical compositions have been described. The descriptions and examples are intended to be illustrative of the invention and not limiting. Indeed, it will be apparent to those of skill in the art that modifications to the pharmaceutical compositions can be made to the various embodiments of the invention described without departing from the spirit of the invention.

In one aspect the G-CSF or hG-CSF analog compositions can be administered parenterally, for example, subcutaneously or intravenously. The parenteral administration can be in a single bolus or as a continuous infusion. In one aspect, the parenteral administration can be a single intravenous infusion given over 15-30 minutes. In another aspect the parenteral administration can be a continuous infusion of G-CSF or hG-CSF analog diluted in 5% dextrose.

The methods provide for administration of G-CSF or hG-CSF analog for a therapeutically or prophylactically effective time. In certain embodiments, the G-CSF or hG-CSF analog is administered prior to the onset or observation of the disorder or symptoms accompanying the disorder. In further embodiments, the G-CSF or hG-CSF analog is administered during the disorder or during the time period that symptoms accompanying the disorder are observed. In other embodiments, the G-CSF or hG-CSF analog is administered for a time after the disorder had cleared. For example, the G-CSF or hG-CSF analog can be administered about one day, about two days, about three days, about four days, about one week, about two weeks and up to about eight weeks, following resolution of threatened abortion or after confirmation of pregnancy during assisted reproduction.

Diagnostic Assays

While generally a medical history will serve to ascertain candidate subjects in need of treatments as described above, diagnostic assays can be used to ascertain subjects presented with reproductive inefficiencies that are correlated with particular immunologic parameters. As noted herein, patients with repeated spontaneous abortion, miscarriage, or implantation failure and the like present with particular profiles of their immune system status. Thus, subjects with high Th1 cell number or cell activity and/or reduced Th2 cell number or cell activity, or an aberrant ratio of the two may be candidates for obtaining the above-described treatment.

Hence, a diagnostic assay of interest is one that determines whether Th1 cell number or cell activity is enhanced. Another assay of interest is one that determines whether Th2 cell number or activity is decreased. Yet another assay of interest is one that determines a higher ratio of Th1 cell number to Th2 cell number, or Th1 cell activity to Th2 cell activity.

A number of known assays, for example, immunoassays or bioassays, can be used to make such determinations. For example, γ interferon, tumor necrosis factor alpha, tumor necrosis factor β, IL-2, IL-12, and IL-18 are markers of Th1 cells. Thus, assays for one or more of such cell-specific markers can provide the basis to conclude a higher than normal Th1 status. As to Th2, IL-4, IL-5, IL-6, IL-10 and IL-13 are known markers of that cell type. Thus, assays for one or more of such cell-specific markers can provide the basis to conclude a higher than normal Th2 status.

Diagnostic assays can be also used to ascertain subjects presenting with reproductive inefficiencies that are correlated with particular pathophysiologic parameters. Pathophysiologic markers could include markers of cell stress such as heat shock proteins, markers of oxidative stress such as nitric oxide and free radicals, markers of cell injury such as hepatic transaminases and creatine kinase, and markers of cell death including caspase 1 & 3.

In other embodiments, a diagnostic kit can be used to ascertain subjects presenting with reproductive inefficiencies that are correlated with serum or ovarian follicular fluid G-CSF concentrations. Such a kit would serve as a theranostic complimenting G-CSF as a therapeutic.

Kits

In another aspect, the present invention provides kits for carrying out the methods of the invention. In certain embodiments, the present invention provides kits for preventing or reducing the likelihood of spontaneous abortion, implantation failure, preeclampsia and preterm labor during and following a FET, ICSI, GIFT or ZIFT procedure. The kits comprise one or more effective doses of G-CSF or hG-CSF analog along with a label or labeling with instructions on using the G-CSF or hG-CSF analog to prevent or reduce the likelihood of spontaneous abortion, implantation failure, preeclampsia and preterm labor during and following a FET, ICSI, GIFT or ZIFT procedure according to the methods of the invention. In certain embodiments, the kits can comprise components useful for carrying out the methods such as devices for delivering the G-CSF. In certain embodiments, the kit can comprise components useful for the safe disposal of devices for delivering the G-CSF or hG-CSF analog, e.g., a sharps container for used syringes.

In one embodiment, the G-CSF or hG-CSF analog in the kit is formulated for subcutaneous administration. In another embodiment, the G-CSF or hG-CSF analog in the kit is formulated for intramuscular administration. In another embodiment, the G-CSF or hG-CSF analog in the kit is formulated for intravascular administration.

The kit may further contain other active compounds, such as CSFs (e.g., G-CSF, GMCSF, and macrophage CSF), erythropoietin, stem cell factors, anti-inflammatory agents, interleukins, etc.

In one embodiment, the G-CSF or hG-CSF analog in the kit is contained in an implantable device for slow release after implantation of the device. In another embodiment, the G-CSF or hG-CSF analog in the kit is contained in a transdermal patch for slow release after application of the transdermal device.

In another embodiment, the present invention provides a transdermal patch comprising G-CSF or hG-CSF analog as an active ingredient. In another embodiment, the present invention provides an implantable device comprising G-CSF or hG-CSF analog as an active ingredient. In yet another embodiment, the present invention provides an implantable device with G-CSF or hG-CSF analog embedded in an inert matrix.

In another embodiment, the present invention provides a vaginal ring comprising G-CSF or hG-CSF analog as an active ingredient and in some cases with another complimentary agent as an additional active ingredient.

The present invention is further illustrated by the following examples which should not be construed as limiting. The contents of all references, patents and published patent applications cited throughout this application, as well as the Figures and Tables are incorporated herein by reference.

Example 1

G-CSF Prevents Embryotoxic Effects of Cells from Women with Recurrent Spontaneous Abortion In Vitro G-CSF is effective in preventing the death of mouse embryos in an in vitro clinical assay for spontaneous abortion. Mouse bioassays have widely been used to detect embryotoxic effects of sera from subjects having reproductive difficulty. (See, Cameo, et al., 1999, Human Reprod. 14(4):959-63, Oksenberg and Brautbar 1986, Am. J. Reprod Immunol. Microbiol. 11(4):118-24, Roussev et al., 1995, Am. Reprod. Immunol. 33(2):171475 and Thomason et al., 1995, Am. J. Reprod. Immunol. 34(6):338-41.).

In the in vitro clinical assay, mononuclear leukocytes are isolated from women suffering from recurrent spontaneous abortion. The leukocytes are cultured, and the culture medium is removed from the leukocytes. This culture medium is then contacted with murine embryos. Toxic factors in the culture medium typically kill the murine embryos in this assay.

The mononuclear leukocytes are incubated with G-CSF prior to removal of the culture medium. The culture medium is then removed from the leukocytes and contacted with murine embryos. Survival of the murine embryos indicates the reduction of embryotoxic factors in the culture medium and thereby the effectiveness of G-CSF administration for prevention of spontaneous abortion in this in vitro model.

Example 2

G-CSF Prevents Spontaneous Abortion in a Mouse Model In Vitro

G-CSF effectively inhibits a well-known in vivo model for spontaneous abortion.

The murine mating pair CBA×DBA/2 (see e.g., Yabuki et al., 2003, Exp. Anim. 52 (2) 159-63) results in a spontaneous abortion rate of approximately 40%. In this example, female CBA mice are treated according to the methods of the invention. They are treated with G-CSF prior to mating, at the time of mating and immediately after mating. A reduction of the rate of spontaneous abortion in mice treated with G-CSF relative to control mice indicates that G-CSF effectively prevents spontaneous abortion in this in vivo model.

Example 3

Patients' Case Studies

Over the course of the last several years, three patients undergoing assisted reproduction procedures have been treated with recombinant hG-CSF (rhG-CSF). Case studies of these three patients are provided below.

(1) J. C.

J. C. is a 36-year-old married white female with an obstetrical history of three uncomplicated vaginal deliveries at full term (all male children) followed by six consecutive first trimester miscarriages (each at 10-12 weeks). Conception was natural in each of the successful pregnancies and in each miscarriage. Each miscarried fetus was karyotyped, and all were normal. The couple then experienced three years of secondary infertility. At that point, she sought a consultation with a reproductive endocrinologist (RE).

The RE performed a detailed workup to attempt to identify the cause of the couple's reproductive failures. No anatomic or endocrinologic etiology was identified. Both J. C. and her husband were found to be karyotypically normal. A standard andrology workup for the husband was negative.

J. C.'s past medical history was significant in that J. C. had a remote past history of seasonal allergies and ten years of allergy desensitization shots. Based on this medical history, a series of immunologic tests including measurement of Th1 and Th2 cytokine production in vitro were ordered. As noted previously in this application, allergy is a classic Th2 immunopathologic response. Although few allergists realize it, allergy desensitization works by presenting the allergen in a manner that favors Th1 cytokine production instead of Th2 cytokine production. In many individuals, this shift from Th2 to Th1 dominance becomes more generalized and antigen non-specific. The series of tests ordered for J. C. specifically measured Th1/Th2 cytokines produced by the patient's peripheral blood mononuclear cells (PBMC) in response to the non-specific mitogen phytohemagglutinin (PHA). J. C.'s PBMC produced greater than 10,000 units per ml of the prototypic Th1 cytokine gamma interferon in response to PHA. Levels of the prototypic Th2 cytokine IL-4 and the counter regulatory Th2 cytokine IL-10 were undetectable.

The RE performed intrauterine insemination (IUD using J. C.'s husband's sperm. The first attempt at IUI resulted in a positive HCG at 7 days. The rhG-CSF administration was initiated the following day. The regimen consisted of 100 mcg/day of rhG-CSF (Neupogen) injected subcutaneously for a total of 30 days, a cumulative dose of 3000 mcg. The rhG-CSF regimen was carried out for the full 30 days and then discontinued. The patient experienced no rhG-CSF-related side effects at any point during the regimen.

At day 14 of the rhG-CSF regimen, another blood sample was obtained from J. C. for repeat measurement of Th1 and Th2 cytokines by her PBMC in response to PHA. The repeat results showed undetectable levels of the prototypic Th1 cytokine gamma interferon and elevated levels (2,000 units per ml) of the counter regulatory Th2 cytokine IL-10. These results clearly indicated that rhG-CSF produced a shift from Th1 to Th2 cytokine production by her PBMC in response to PHA. Interestingly, J. C.'s allergies had also returned. This is consistent with the shift from Th1 to Th2 cytokine dominance.

At 8 weeks, an ultrasound confirmed an ongoing healthy pregnancy with a well-formed gestational sac and a fetus with a strong heartbeat. The pregnancy continued to progress uneventfully and at 11 weeks J. C. was transferred from the care of her RE to the care of a general obstetrician. The pregnancy progressed without complication, and a healthy 8 lb., 19-inch female was delivered by planned cesarean section at 38 weeks. Mother and child are both doing well.

(2) N. C.

N. C. is a healthy 35-year-old married white female with an obstetrical history of primary infertility including three failed IUIs and one failed IVF.

N. C.'s first IUI resulted in monozygotic twins, one of which revealed no fetal heartbeat at 6 weeks and the other which had a confirmed weak fetal heartbeat at 6 weeks but no heartbeat by the 7$^{th}$ week. The second IUI resulted in a singleton pregnancy and fetal demise at 8 weeks. A heartbeat was seen at the 7$^{th}$ week but was negative by the 8$^{th}$ week. Karyotyping was performed and revealed an abnormal karyotype (69 XXY). N. C.'s third IUI resulted in a probable ectopic pregnancy treated with methotrexate. N. C.'s last pregnancy attempt was a cycle of IVF. This resulted in a confirmed and apparently healthy pregnancy at 6 weeks with a gestational sac measuring 36×37 millimeters and fetal heart rate of 113. However, one week later no fetal heartbeat was observed. The products of conception were expelled in large clots, and karyotyping was performed. Karyotyping was revealed to be normal (46 XY). N. C.'s RE performed an exhaustive workup to determine the cause of her reproductive failures. However, the workup failed to reveal any identifiable cause.

N. C.'s past medical history was non-contributory. She appeared to be a healthy female with unexplained primary infertility and repeated pregnancy loss. A review of her medical records revealed past laboratory testing showed a normal balance of Th1 and Th2 cytokines.

Because one of N. C.'s early losses involved a karyotypically abnormal embryo (69 XXY), N. C. had arranged for preimplantation genetic diagnosis for her last (failed) IVF cycle. N. C. had two cryopreserved embryos left from that cycle, and those embryos were used for the IVF cycle with rhG-CSF. N. C. received 100 mcg per day for the seven days prior to transfer and for 30 additional days after transfer, at a cumulative dose of 3700 mcg. N. C. experienced no rhG-CSF related side effects. At 6 weeks an ultrasound evaluation of N. C. revealed a healthy pregnancy with a well-formed gestational sac (40×40 mm) and a strong heart beat (145 beats per minute). At the 10th week, N. C. was transferred from her RE's care to the high-risk obstetrical unit in a hospital where she delivered a healthy baby boy. Both mother and child are doing well.

Approximately one year later, N. C. opted to undergo another IVF cycle at a different clinic without the benefit of rhG-CSF therapy. This cycle failed and was classified as a biochemical pregnancy (positive beta HCG, no evidence of gestational sac or embryo).

A few months later, N. C. contacted the inventor to request that he provide consultation regarding the use of rhG-CSF in her next IVF cycle. The inventor agreed and a clinical plan identical to her previous IVF cycle using rhG-CSF was pursued. N. C. began rhG-CSF (100 mcg per day) five days prior to embryo transfer (i.e., on the day of oocyte retrieval) in a fresh IVF cycle. The pregnancy is ongoing and her RE has transferred her to the care of a general obstetrician. At her last examination (at 20 weeks), all measurements were normal for gestational age and fetal heartbeat was strong.

(3) J. J.

J. J. is a 33-year-old married white female with a history of primary subfertility and seven failed pregnancies. Over a period of three years, J. J. suffered three first-trimester miscarriages and three chemical pregnancies. Four of the pregnancies involved the use of fertility drugs and natural conception. Two of the pregnancies occurred through IUI. The last pregnancy was a failed cycle of IVF.

J. J.'s RE performed a standard workup to attempt to determine cause for J. J.'s failures. The workup failed to identify a cause. Both members of the couple were found to be karyotypically normal. J. J. and her RE decided that she should consult with a Reproductive Immunologist. Prior to J. J.'s IVF cycle, this physician performed a battery of laboratory tests and a medical evaluation and concluded that J. J. should undergo a course of Intravenous Immunoglobulin (IVIG) to correct immune problems identified through testing. Repeat laboratory tests demonstrated that WIG failed to correct the purported immunologic problem. J. J.'s IVF cycle resulted in an ectopic pregnancy, and J. J. required emergency surgery for a unilateral salpingectomy.

J. J. and her RE sought a consultation with the inventor and decided to undergo another cycle of IVF with rhG-CSF treatment.

J. J. underwent another cycle of IVF with frozen embryos from her previous cycle. Although J. J. was scheduled to begin rhG-CSF at 100 mcg per day five days prior to embryo transfer, J. J. was not able to begin rhG-CSF until three days before embryo transfer. The rhG-CSF was continued at 100 mcg per day for 30 days after embryo transfer. The cumulative dose of rhG-CSF was 3300 mcg. J. J. completed her course of rhG-CSF and experienced no rhG-CSF related side effects.

Two embryos were transferred. The cycle resulted in a positive beta HCG (139 at 7 days post transfer; 316 at 10 days post transfer). Six weeks post transfer, an ultrasound identified a well-formed gestational sac and a heart beat of 115.

J. J. underwent another ultrasonic evaluation at 10 weeks gestation, and a strong heartbeat was identified and all measurements were exactly appropriate for dates. J. J. was transferred to the care of a general obstetrician and delivered a healthy baby girl. Both the mother and the child are healthy and doing well.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for reducing the risk of spontaneous abortion in a human female recipient of an assisted reproduction procedure, comprising administering to the recipient during the first twenty weeks of pregnancy an effective amount of a composition comprising granulocyte colony stimulating factor (G-CSF), wherein G-CSF is administered at a dose of 1 mcg/kg/day to 100 mcg/kg/day, wherein said female recipient has the risk of spontaneous abortion.

2. The method of claim 1, wherein said composition is administered parenterally.

3. The method of claim 1, wherein said composition is administered enterally.

4. The method of claim 1, wherein said composition is administered topically.

5. The method of claim 1, wherein said composition is administered by inhalation.

6. The method of claim 1, wherein said composition is administered daily.

7. The method of claim 1, wherein said assisted reproduction procedure is gamete intra-fallopian transfer (GIFT).

8. The method of claim 1, wherein said composition is administered for one day, two days, three days or four days.

9. The method of claim 1, wherein said composition is administered daily for one week.

10. The method of claim 1, wherein said composition is administered daily for two weeks.

SEQUENCE LISTING

```
<160> NUMBER OF SEQ ID NOS: 1

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

11. The method of claim 1, wherein said G-CSF is administered at a dose of between 1 mcg/kg/day to 20 mcg/kg/day.

12. The method of claim 1, wherein said composition further comprises an additive.

13. The method of claim 12, wherein said additive comprises an immunosuppressive agent.

14. The method of claim 13, wherein said immunosuppressive agent comprises vitamin D3 (1,25 dihydroxycholecalciferol), analogs thereof, or corticosteroids.

15. The method of claim 1, wherein said composition further comprises a pharmaceutically acceptable carrier.

16. The method of claim 1, wherein said human female recipient previously had one or more spontaneous abortions, two or more spontaneous abortions, or recurrent spontaneous abortions.

17. The method of claim 1, wherein said human female recipient is in the first trimester of pregnancy, or is in the first or second month of pregnancy.

18. The method of claim 1, wherein said dose is administered daily for four, three, two or one week during the first trimester of pregnancy.

19. The method of claim 1, wherein said dose is administered for at least five consecutive days during the first or second trimester of pregnancy, or for at least five consecutive days during the first or second week of pregnancy.

* * * * *